US009224312B2

(12) United States Patent
Martin et al.

(10) Patent No.: US 9,224,312 B2
(45) Date of Patent: Dec. 29, 2015

(54) METHODS AND DEVICES FOR DETERMINING SENSING DEVICE USABILITY

(75) Inventors: Glenn Martin, Ottawa (CA); Tian-Xian Zhao, Ottawa (CA); Steven Breeze, Ottawa (CA); Craig Jeffrey, Ottawa (CA); Stephen Lee Snyder, Ottawa (CA)

(73) Assignee: Abbott Point of Care Inc., Princeton, NJ (US)

( * ) Notice: Subject to any disclaimer, the term of this patent is extended or adjusted under 35 U.S.C. 154(b) by 683 days.

(21) Appl. No.: 13/538,148

(22) Filed: Jun. 29, 2012

(65) Prior Publication Data

US 2013/0002279 A1 Jan. 3, 2013

Related U.S. Application Data

(60) Provisional application No. 61/503,234, filed on Jun. 30, 2011.

(51) Int. Cl.
*G01R 31/3187* (2006.01)
*B05D 5/12* (2006.01)
*G01N 27/20* (2006.01)
*G09F 3/00* (2006.01)
*G01N 27/327* (2006.01)

(52) U.S. Cl.
CPC .......... *G09F 3/0291* (2013.01); *G01N 27/3274* (2013.01)

(58) Field of Classification Search
CPC ................................. G01N 27/3274
See application file for complete search history.

(56) References Cited

U.S. PATENT DOCUMENTS

| 3,922,431 A | * | 11/1975 | Radmacher et al. ........... 428/327 |
| 3,942,467 A | | 3/1976 | Witonsky |
| 3,983,527 A | | 9/1976 | Ohsato et al. |
| 4,059,406 A | | 11/1977 | Fleet |
| 5,096,669 A | | 3/1992 | Lauks et al. |
| 5,209,931 A | * | 5/1993 | Levin ........................... 424/405 |
| 5,273,640 A | | 12/1993 | Kusanagi et al. |

(Continued)

FOREIGN PATENT DOCUMENTS

| CN | 1427770 A | 7/2003 |
| CN | 101815936 A | 8/2010 |

(Continued)

OTHER PUBLICATIONS

Office Action for Chinese Application No. 201280039926.0 dated Oct. 13, 2014.

(Continued)

*Primary Examiner* — Patrick Assouad
*Assistant Examiner* — Haidong Zhang

(57) ABSTRACT

Methods and devices for determining sensing device usability, e.g., for point of care immunoassay devices. In one embodiment, the invention is to a method of determining device usability, comprising the steps of providing a device comprising a first electrical pad; a second electrical pad; and a continuous polymer layer contacting at least a portion of the first and second electrical pads; applying a potential across the first and second electrical pads; measuring an electrical property associated with the continuous polymer layer; and determining whether the measured electrical property associated with the continuous polymer layer has exceeded a threshold level associated with the device usability.

39 Claims, 15 Drawing Sheets

(56) References Cited

U.S. PATENT DOCUMENTS

| | | | |
|---|---|---|---|
| 5,554,339 | A | 9/1996 | Cozzette et al. |
| 6,063,486 | A | 5/2000 | Kobayashi |
| 6,158,381 | A | 12/2000 | Bray |
| 6,544,925 | B1 | 4/2003 | Prusik et al. |
| 6,629,057 | B2 | 9/2003 | Zweig et al. |
| 7,418,285 | B2 | 8/2008 | Ghesquiere et al. |
| 7,612,325 | B1* | 11/2009 | Watkins et al. ............ 250/222.2 |
| 7,723,099 | B2 | 5/2010 | Miller et al. |
| 8,835,180 | B2 | 9/2014 | Gryska et al. |
| 2003/0139903 | A1 | 7/2003 | Zweig et al. |
| 2003/0148530 | A1 | 8/2003 | Lauks |
| 2004/0256227 | A1 | 12/2004 | Shin et al. |
| 2006/0214312 | A1 | 9/2006 | Wu et al. |
| 2007/0132542 | A1 | 6/2007 | Beck et al. |
| 2007/0166831 | A1 | 7/2007 | Watkins, Jr. et al. |
| 2008/0145277 | A1 | 6/2008 | Wohland |
| 2009/0022630 | A1 | 1/2009 | Hoenes et al. |
| 2009/0056644 | A1 | 3/2009 | Phillips et al. |
| 2009/0119047 | A1* | 5/2009 | Zelin et al. ...................... 702/82 |
| 2009/0159442 | A1* | 6/2009 | Collier et al. ............. 204/403.1 |
| 2009/0182244 | A1 | 7/2009 | Hoenes |
| 2009/0184004 | A1* | 7/2009 | Chatelier et al. .......... 205/777.5 |
| 2010/0206749 | A1 | 8/2010 | Choi et al. |
| 2011/0105613 | A1 | 5/2011 | Reiner et al. |
| 2011/0155043 | A1 | 6/2011 | Haarer et al. |
| 2013/0000378 | A1 | 1/2013 | Martin et al. |
| 2013/0002265 | A1 | 1/2013 | Martin et al. |
| 2013/0002278 | A1 | 1/2013 | Martin et al. |

FOREIGN PATENT DOCUMENTS

| | | |
|---|---|---|
| EP | 2098857 | 9/2009 |
| WO | WO 2009/036429 | 3/2009 |
| WO | 2009/156285 A1 | 12/2009 |

OTHER PUBLICATIONS

International Preliminary Report on Patentability for PCT/US2012/044919 mailed Jan. 16, 2014.
International Preliminary Report on Patentability for PCT/US2012/044909 mailed Jan. 16, 2014.
International Preliminary Report on Patentability for PCT/US2012/044905 mailed Jan. 16, 2014.
International Preliminary Report on Patentability for PCT/US2012/044898 mailed Jan. 16, 2014.
Office Action for U.S. Appl. No. 13/537,983 dated Jul. 31, 2014.
Office Action for U.S. Appl. No. 13/538,218 dated Oct. 2, 2014.
I-STAT System Manuel (2004) Abbott Point of Care.
Heller, et al., "Electrochemical Glucose Sensors and Their Applications in Diabetes Management", Chem. Rev. 2008, pp. 2482-2505.
International Search Report and Written Opinion for PCT/US2012/044919 mailed Oct. 5, 2012.
International Search Report and Written Opinion for PCT/US2012/044909 mailed Oct. 5, 2012.
International Search Report and Written Opinion for PCT/US2012/044905 mailed Oct. 5, 2012.
International Search Report and Written Opinion for PCT/US2012/044898 mailed Oct. 5, 2012.
U.S. Appl. No. 13/537,983, Final Office Action, dated May 1, 2015, 11 pages.
State Intellectual Property Office of the People's Republic of China, Second Office Action, Application No. 201280039926, dated Jun. 26, 2015.
First Office Action mailed Sep. 22, 2014 in CN Patent Application No. 201280039929.4, 14 pages.
Final Office Action mailed Apr. 15, 2015 in U.S. Appl. No. 13/538,218, 14 pages.
Notice of Allowance mailed on Aug. 10, 2015 for U.S. Appl. No. 13/537,983, 8 pages.

* cited by examiner

FIG. 2

Initial TTI Formulations

| Formulation | Plasticizer | PVC | ETH-500 (% Solids) | Plasticizer:PVC |
|---|---|---|---|---|
| 1 | TOP | LMW | 2 | 50:50 |
| 2 | TOP | LMW | 2 | 66:33 |
| 3 | TOP | HMW | 2 | 80:20 |
| 4 | TOP | LMW | 5 | 66:33 |
| 5 | NPOE | LMW | 2 | 66:33 |
| 6 | BEHS | LMW | 2 | 66:33 |

Formulations Evaluated

| Formulation | ETH-500 (% Solids) | TOP:BEHS:PVC |
|---|---|---|
| A | 7 | 66 : 00 : 33 |
| B | 5 | 33 : 33 : 33 |
| C | 7 | 33 : 33 : 33 |

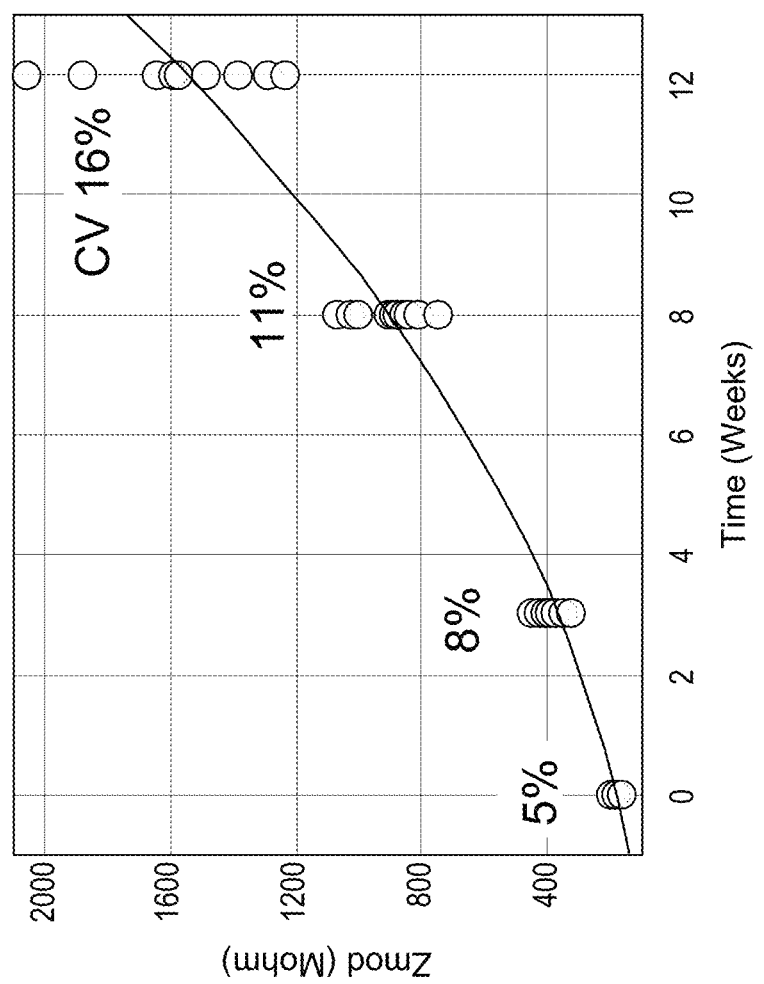

METHODS AND DEVICES FOR DETERMINING SENSING DEVICE USABILITY

CROSS REFERENCE TO RELATED APPLICATIONS

This application claims priority to U.S. Provisional Application No. 61/503,234 filed on Jun. 30, 2011, the entirety of which is incorporated herein by reference.

FIELD OF THE INVENTION

The present invention relates to a method of determining device usability through the application of a potential across a continuous polymer matrix and measuring an electrical property to determine whether a device has exceeded a threshold level associated with device usability.

BACKGROUND OF THE INVENTION

A multitude of laboratory immunoassay tests for analytes of interest are performed on biological samples for diagnosis, screening, disease staging, forensic analysis, pregnancy testing and drug testing, among others. While a few qualitative tests, such as pregnancy tests, have been reduced to simple kits for a patient's home use, the majority of quantitative tests still require the expertise of trained technicians in a laboratory setting using sophisticated instruments. Laboratory testing increases the cost of analysis and delays the patient's receipt of the results. In many circumstances, this delay can be detrimental to the patient's condition or prognosis, such as for example the analysis of markers indicating myocardial infarction and heart failure. In these and similar critical situations, it is advantageous to perform such analyses at the point-of-care, accurately, inexpensively and with minimal delay.

Point-of-care sample analysis systems are generally based on a reusable reading apparatus that performs sample tests using a disposable device (e.g., a cartridge or strip) that contains analytical elements (e.g., electrodes or optics for sensing analytes such as, for example, pH, oxygen, or glucose). The disposable device can optionally include fluidic elements (e.g., conduits for receiving and delivering the sample to the electrodes or optics), calibrant elements (e.g., fluids for standardizing the electrodes with a known concentration of the analyte), and dyes with known extinction coefficients for standardizing optics.

Point-of-care sample testing systems eliminate the time-consuming need to send a sample to a central laboratory for testing. Point-of-care sample testing systems allow a user e.g. a nurse and physician, at the bedside of a patient, to obtain a reliable, quantitative, analytical results, comparable in quality to that which would be obtained in a laboratory. In operation, the user may select a device with the required panel of tests (e.g., electrolytes, metabolites, cardiac markers and the like), draw a sample, dispense it into the device, optionally seal the device, and insert the device into the reading apparatus to communicate the data to an LIS/HIS for analysis. An example of such a system is the i-STAT® system sold by Abbott Point-of-Care, Inc., Princeton, N.J., USA. The i-STAT® portable blood analysis system typically comprises Wi-Fi-enabled reader instruments that work in conjunction with single-use blood testing cartridges that contain sensors for various analytes. For further information on the i-STAT® portable blood analysis system, see http://www.abbotpointofcare.com/.

Analyzers, such as a self-contained disposable sensing device or cartridge and a reader or instrument, are further described in commonly owned U.S. Pat. No. 5,096,669 to Lauks, et al., the entirety of which is incorporated herein by reference. In operation, a fluid sample to be measured is drawn into a device and the device is inserted into the reader through a slotted opening. Data generated from measurements performed by the reader may be output to a display and/or other output device, such as a printer, or, as described in greater detail below, via a wireless network connection. The disposable device may contain sensing arrays and several cavities and conduits that perform sample collection, provide reagents for use in measurement and sensor calibration, and transport fluids to and from the sensors. Optionally, reagents may be mixed into the sample for testing. Sensing arrays in the device measure the specific chemical species in the fluid sample being tested. The electrochemical sensors are exposed to and react with the fluid sample to be measured generating electrical currents and potentials indicative of the measurements being performed. The electrochemical sensors may be constructed dry and when the calibrant fluid flows over the electrochemical sensors, the sensors easily "wet up" and are operational and stable for calibration and composition measurements. These characteristics provide many packaging and storage advantages, including a long shelf life. Each of the sensing arrays may comprise an array of conventional electrical contacts, an array of electrochemical sensors, and circuitry for connecting individual sensors to individual contacts. The electrical signals are communicated to a reader enabled to perform calculations and to display data, such as the concentration of the results of the measurement.

Although the particular order in which the sampling and analytical steps occur may vary between different point-of-care systems and providers, the objective of providing rapid sample test results in close proximity to a patient remains. The reading apparatus (e.g., i-STAT® or other wireless analyzer) may then perform a test cycle (i.e., all the other analytical steps required to perform the tests). Such simplicity gives the physician quicker insight into a patient's physiological status and, by reducing the time for diagnosis, enables a quicker decision by the physician on the appropriate treatment, thus enhancing the likelihood of a successful patient treatment.

In the emergency room and other acute-care locations within a hospital, the types of sample tests required for individual patients can vary widely. Thus, point-of-care systems generally offer a range of disposable devices configured to perform different sample tests, or combinations of such tests. For example, for blood analysis devices, in addition to traditional blood tests, including oxygen, carbon dioxide, pH, potassium, sodium, magnesium, calcium, chloride, phosphate, hematocrit, glucose, urea (e.g., BUN), creatinine and liver enzymes, other tests may include, for example, prothrombin time (PT), activated clotting time (ACT), activated partial thromboplastin time (APTT), troponin, creatine kinase MB (CKMB), and lactate. Although devices typically contain between one and ten tests, it will be appreciated by persons of ordinary skill in the art that any number of tests may be contained in a device.

A given hospital may use numerous different types of test devices and test instruments at multiple point-of-care testing locations within the hospital. These locations can include, for example, an emergency room (ER), a critical care unit (CCU), a pediatric intensive care unit (PICU), an intensive care unit (ICU), a renal dialysis unit (RDU), an operating room (OR), a cardiovascular operating room (CVOR), general wards (GW), and the like. Other non-hospital-based locations where medical care is delivered, include, for example, MASH units, nursing homes, and cruise, commercial, and military ships.

In some cases, cartridges have a shelf life which may vary widely depending on the specific cartridge as well as upon storage conditions. For example, some cartridges may have a shelf life of about six to about nine months when refrigerated, but a much more limited shelf life, e.g., about two weeks at room temperature, or, more specifically, about ten weeks at up to about 30° C. As a result, hospitals typically store cartridges at a central refrigerated location, and deliver cartridges to specific locations as demand requires. These locations can include, for example, an emergency room (ER), critical care unit (CCU), pediatric intensive care unit (PICU), intensive care unit (ICU), renal dialysis unit (RDU), operating room (OR), cardiovascular operating room (CVOR) and general wards (GW). These locations may or may not have available refrigerated storage, and this will impact product lifetime and, as a result, the inventory they will hold. Further complicating device management is the fact that a given user, such as a hospital, may use multiple types of cartridges, each having a different shelf life. Alternatively, the user may be a physician's office laboratory or visiting nurse service. However, the need to ensure quality remains the same.

U.S. Patent Appl. No. US 2009/0119047 to Zelin et al., the entirety of which is incorporated herein by reference, discloses an improved quality assurance system and method for point-of-care testing. It provides quality assurance for laboratory quality tests performed by a blood analysis system at the point of patient care without the need for running liquid-based quality control materials on the analysis system. Quality assurance of a quantitative physiological sample test system is performed without using a quality control sample by monitoring the thermal and temporal stress of a component used with the test system. Alert information is generated that indicates that the component has failed quality assurance when the thermal and temporal stress exceeds a predetermined thermal-temporal stress threshold.

U.S. Pat. No. 7,612,325 to Watkins Jr., et al., the entirety of which is incorporated herein by reference, discloses electrical sensor for monitoring degradation of products from environmental stressors and describes an environmental degradation sensor for environmentally sensitive products such as food, pharmaceuticals or cosmetic products provides the degraded state and estimated remaining life of the product. The sensor is made of a polymeric matrix and conductive filler. A control agent, selected to adjust a reaction rate of the sensor to environmental conditions, allows correlation of an electrical property of the sensor to a degraded state of the product.

In general, the principles of operation for existing types of time/temperature indicators can be categorized as physical, chemical and electrical. Examples of physical and chemical methods include color change of polymeric materials, chemical reactions of two elements, physical masking of a marker, melting of a temperature sensitive material and the like.

However, the use of many existing indicators adds significant cost and complexity to the devices they are intended to monitor. This is a particularly apparent issue for single-use blood testing cartridges and electrochemical strip devices, e.g., glucose blood testing strips used by diabetics. Consequently, the need remains for improved low cost time-temperature indicators that are amenable to direct integration into a device manufacturing work flow.

SUMMARY OF THE INVENTION

In one embodiment, the invention is to a method of determining device usability, comprising the steps of: providing a device comprising a first electrical pad; a second electrical pad; and a continuous polymer layer contacting at least a portion of the first and second electrical pads; applying a potential across the first and second electrical pads; measuring an electrical property, e.g., current, resistance, impedance, conductivity, or a combination thereof, associated with the continuous polymer layer; and determining whether the measured electrical property associated with the continuous polymer layer has exceeded a threshold level associated with the device usability. Optionally, the method further comprises a step of measuring an initial current value associated with the continuous polymer layer when the device is manufactured and wherein the threshold level is at least five times lower than the initial current value. As an alternative, the method may include a step of measuring an initial impedance value associated with the continuous polymer layer when the device is manufactured, wherein the threshold level is at least five times greater than the initial impedance.

In one aspect, the potential comprises a sigmoidal potential cycle, a fixed applied potential, a sequence of fixed applied potential steps, or a combination thereof. The potential optionally comprises a potential cycle that is applied at a predetermined frequency in the range of about 1 Hz to about 100 Hz. The method optionally includes a step of inserting the device into an analyzer configured to determine whether the measured electrical property associated with the continuous polymer layer has exceeded the threshold level associated with the device usability.

In another embodiment, the invention is to a device having a usability threshold, comprising a first electrical pad, a second electrical pad, and a continuous polymer layer contacting at least a portion of the first and second electrical pads, wherein the continuous polymer layer has an electrical property associated with the device usability threshold.

In another embodiment, the invention is to a device comprising a continuous polymer layer formed on a substantially planar surface wherein the surface comprises two adjacent electrical contact pads having a space therebetween, said polymer layer covering at least a portion of the two electrical contact pads and a portion of the space therebetween, wherein when a preselected potential or potential cycle is applied to the pads and the impedance or current associated with said polymer layer is measured, said measured value determines whether or how the device is used.

In another embodiment, the invention is to a device comprising a sensor and a continuous polymer layer formed on a substantially planar surface wherein the surface comprises two adjacent electrical contact pads and a space therebetween, wherein said polymer layer covers at least a portion of the two electrical contact pads and a portion of said space therebetween, wherein a preselected potential or potential cycle is applied to the pads and the impedance or current associated with said polymer layer is measured, said measured value is converted to a value indicative of the average shelf life time remaining for other devices from the same manufacturing lot.

In preferred embodiments, the polymer layer comprises a polymer matrix, a plasticizer and an organic salt. For example, the polymer layer may comprise from 20 to 40 wt. % polymer matrix. The polymer matrix may comprise a polymer selected from the group consisting of polyvinyl chloride, polyurethane, polyvinylacetate, carboxylated PVC, hydroxylated PVC and polydimethyl siloxane. The polymer layer optionally comprises from 60 to 80% plasticizer, which may be selected from the group consisting of trioctyl phosphate (TOP), nitrophenyloctyl ether (NPOE), bisethylhexylsebacate (BEHS), trimethyl trimellitate (TMTT), dioctyl adipate (DOA) and diisobutyl phthalate (DIBP). The polymer layer may comprise from 0.1 to 10 wt. % of an organic or inorganic salt, e.g., a salt selected from the group consisting of quaternary ammonium tetrakis phenylborate, dodecyl sulfosuccinate, lauryl sulfate, alkyl ether phosphates, benzylkonium, cetylpyridinium dodecyl sulfosuccinate, lauryl sulfate, alkyl ether phosphates, tetramethylammonium, benzylkonium, cetylpyridinium, an iodide, a bromide, a perchlorate, a zwitterionic compound, cocamidopropyl hydroxysultaine and quaternary ammonium borate.

The configuration and shape of the polymer layer may vary widely, but in one embodiment, the continuous polymer layer is substantially circular, preferably domed, and has a diameter of from about 20 µm to about 2 mm. The device may further comprise a boundary structure for controlling the spreading of a dispensed polymer layer precursor to a predetermined region of the device, e.g., a ring intersecting said first and second contact pads. The first and second pads optionally are separated by a distance of from about 10 µm to about 2 mm.

The device may comprise a sensor selected from the group consisting of a pH sensor, oxygen sensor, carbon dioxide sensor, hematocrit sensor, glucose sensor, lactate sensor, creatinine sensor, sodium sensor, potassium sensor, magnesium sensor, calcium sensor, chloride sensor, phosphate sensor, liver enzyme sensor, BNP sensor, troponin sensor, BUN sensor, CKMB sensor, NGAL sensor, TSH sensor, D-dimer sensor, PSA sensor, PTH sensor, cholesterol sensor, ALT sensor, AST sensor, prothrombin sensor, APTT sensor, ACT sensor, galectin sensor, and combinations thereof.

In another embodiment, the invention is to a method of making a device having a usability threshold, comprising the steps of providing a substantially planar surface comprising a first electrical pad and a second electrical pad; dispensing a polymer layer precursor onto the surface, and forming from the polymer layer precursor a continuous polymer layer contacting at least a portion of the first and second electrical pads, wherein the continuous polymer layer has an electrical property associated with the device usability threshold. The polymer layer precursor optionally comprises an aqueous solution comprising polymer particles dispersed or dissolved in water or an organic solution comprising polymer particles dispersed or dissolved in an organic solvent.

In another embodiment, the invention is to a method of determining a threshold level associated with analytical device usability, comprising the steps of: providing a plurality of devices, each of said devices comprising a sensor; a first electrical pad; a second electrical pad; and a continuous polymer layer contacting at least a portion of the first and second electrical pads, wherein said devices have been exposed to different environmental conditions; measuring an electrical property of the continuous polymer layer for each of the devices; measuring a sensor signal for a control fluid for each of the devices; identifying a subset of said plurality of devices that provide a signal having a predetermined acceptable precision level for said control fluid; and determining the threshold level that corresponds to the electrical property of the continuous polymer layer for the subset of said plurality of devices. The environmental conditions may, for example, include variations in at least one of time, temperature, or humidity.

BRIEF DESCRIPTION OF THE DRAWINGS

The present invention will be better understood in view of the appended non-limiting figures, in which:

FIGS. 1A presents a diagram and FIG. 2A presents an image showing a continuous polymer layer deposited on first and second electrical pads of a device in accordance with one embodiment of the present invention;

FIG. 2 shows initial formulations for the indicator layers used in Examples 2-4;

DETAILED DESCRIPTION OF THE INVENTION

Figure 1A:
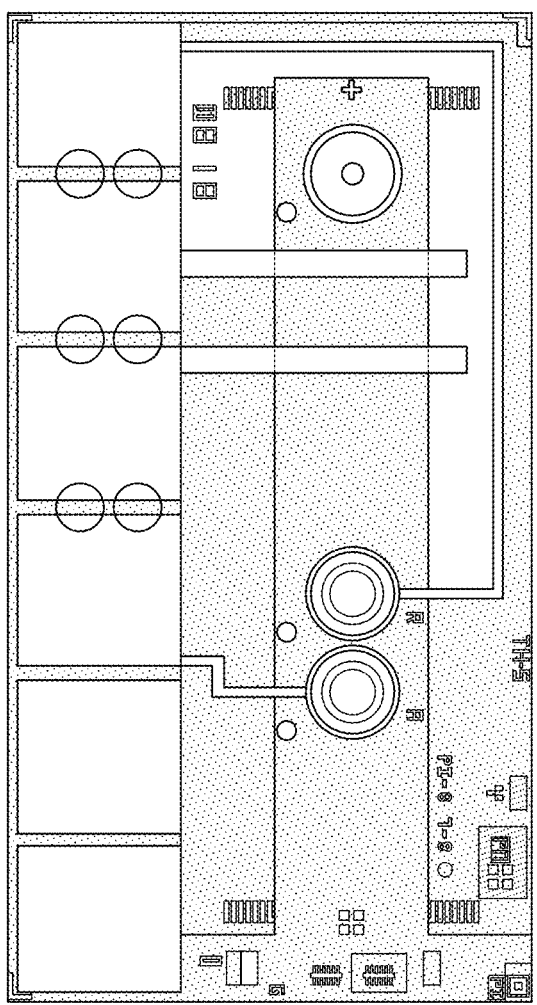

The present invention is best understood in the context of the current prior art on point-of-care blood analysis systems. For example, the shelf life of an i-STAT® cartridge (see the i-STAT® system made by Abbott Point of Care, Princeton, N.J., USA) is typically indicated by a refrigeration expiration date and a room temperature shelf life that are provided on the product packaging, e.g., on a fluid-containing pouch thereof. The refrigeration expiration date defines the length of time that the cartridge may be stored under refrigerated conditions after manufacture, e.g., at about 5° C. Depending on the specific device, the refrigeration expiration date may be about three months, about six months, about nine months or about one year after the date of manufacture. The room temperature shelf life defines the length of time that the cartridge may be stored under room temperature (ambient, e.g., 25° C.) conditions after a cartridge or a box of cartridges is removed from refrigeration conditions, i.e., removed from a refrigerator. The room temperature shelf life should not be allowed to exceed the refrigeration expiration date. The room temperature shelf life is typically on the order of from two to nine weeks, depending on cartridge type. In practice, the room temperature expiration date is calculated from the room temperature shelf life and is written on the box by the user at the time of removal from the fridge. Thus, when a box of cartridges is taken out of the refrigerator, the user typically counts the number of days or months to determine the room temperature expiration date, verifies that the room temperature expiration date does not exceed the refrigeration expiration date printed on the box or cartridge, and writes the room temperature expiration date down on the box. Furthermore, when a cartridge is to be used, the end user again checks the expiry dates. This process lends itself to potential user error in either or both calculating the refrigeration expiration date and/or verifying that the refrigeration expiration date has not been passed. The present invention is intended to determine the suitability of the cartridge for use, i.e., the non-expiration of the shelf life, automatically taking into consideration the age of the device as well as the environment, e.g., temperature, under which the device has been stored. Thus the user is relieved of this task and the opportunity for a user-induced error is diminished.

While there are several time-temperature or shelf life indicators that are known in the art, it is highly desirable to keep the cost and complexity of the device to a minimum. In the present invention this is achieved by providing (or modifying) a pair of electrical contact pads. Many analytical systems employ electrical or electrochemical principles and will already have such electrical contact pads as part of the device. Consequently, their use adds no cost as they are present and necessary for other functions, e.g., are used in analyte detection or in device calibration. The pads are desirably modified so that they can act as shelf life indicators while still fulfilling their intended purpose, typically analyte detection or device calibration. Thus, the function of the TTI of the invention should also be conducted without diminishing the ability or performance of the contact pads for their primary purpose, e.g., signal transmission in analyte sensing or device calibration. It is also contemplated, however, that the electrical contact pads that are used for time/temperature indication according to some embodiments may be separately provided specifically for performing the role of TTI, and do not provide any other role, e.g., in analyte sensing or device calibration. In this latter aspect, separate contact pads optionally may be provided for analyte detection and/or device calibration.

The present invention was in part stimulated by the observation that the electrical resistance of some prototype ion sensor membranes structures was found to change after being incubated at an elevated temperature for certain periods of time. The present invention is thus based on the changing electrical properties, e.g., current flow, resistance and the like, of a polymer layer or the like that is positioned between and preferably contacts two adjacent contact pads. In the present specification, the material that is positioned between the two adjacent contact pads is referred to as a "TTI material." The TTI material is preferably responsive to the integral of varying temperature over time such that this gives rise to a predictable change of its electrical properties.

Devices suitable for use in the present invention include, but are not limited to, point-of-care devices such as those disclosed in U.S. Pat. No. 7,723,099, the entirety of which is incorporated herein by reference. The device preferably comprises a first electrical pad and a second electrical pad in contact with a sensor. As used herein, the term "electrical pad" refers to a location wherein electricity may be applied to the device. The electrical pads of the present invention may, for example, comprise a metal contact comprising gold, silver, a combination thereof or another metal. Suitable sensors for use with the present invention include, but are not limited to, electrochemical sensors, amperometric sensors, potentiometric sensors and conductimetric sensors.

The present invention will be specifically described in the context of an i-STAT cartridge that employs two adjacent hematocrit (Hct) electrode pads, or a Hct pad adjacent to an amperometric sensor pad. Note that, for example, a hematocrit sensor can be used for fluidic integrity checking. Each electrode (or bar) terminates in a contact pad which is used to make contact with the connector in an i-STAT cartridge reader. Features of the connectors are described in jointly owned U.S. Pat. No. 4,954,087, the entirety of which is incorporated herein by reference. As indicated above, the primary functions of integrity checking and hematocrit measurement should not be affected by the additional use of the pads as part of a TTI.

In a preferred embodiment, the present invention thus relates to methods for determining device usability with a time/temperature indicator (TTI). In one embodiment, the method comprises the steps of providing a device comprising a first electrical pad, a second electrical pad, and a TTI material (preferably a continuous polymer layer) contacting at least a portion of the first and second electrical pads; applying a potential across the first and second electrical pads; measuring an electrical property associated with the TTI material; and determining whether the measured electrical property associated with the TTI material has exceeded a threshold level associated with the device usability.

In one aspect, the TTI material is formed by depositing a TTI material precursor between the two contact pads. In a preferred embodiment, the TTI material comprises a continuous polymer layer and the TTI material precursor comprises a polymer layer precursor. The TTI material may be formed by depositing, e.g., printing, the TTI material precursor, e.g., polymer layer precursor, between and preferably overlapping two contact pads, e.g., an amperometric channel pad and a Hct pad or two Hct pads. The TTI material precursor is then optionally treated, e.g., with heat or other radiation, or dried to form the TTI material, e.g., continuous polymer layer, in a region between the two contact pads, and preferably overlapping the contact pads. This configuration enables the reader instrument to measure an electrical property of the TTI material before any sample or calibrant fluid contacts the electrodes, which are located in a fluid conduit within the cartridge. See, for example, jointly owned U.S. Pat. Nos. 5,096,669 and 7,491,821, the entireties of which are incorporated herein by reference. In a preferred embodiment, the electrical property that is measured is the open circuit resistance ($R_{TTI}$) of the TTI material. If the electrical property, e.g., $R_{TTI}$ measurement, does not exceed a predetermined threshold value or is within a certain range, the cartridge is considered valid for use. For such cartridges, depending on how an analyzer is programmed, the analyzer may indicate that the cartridge has expired or otherwise reject the cartridge and abort the test cycle, or engage in another remedial action, e.g., sensor output correction. Nevertheless, it should be understood, however, that such devices may still be suitable for use but may not have the desired degree of clinical precision.

In a preferred embodiment, the step of depositing, e.g., printing, the TTI material precursor between the two pads may be accomplished by using a microdispensing process such as the one described in jointly owned U.S. Pat. No. 5,554,339, the entirety of which is incorporated herein by reference. This process involves preparing a fluid composition suitable for forming the polymer layer and loading it into a microsyringe assembly. The microsyringe assembly may comprise, for example, a reservoir, a microsyringe needle, a pump for delivering the TTI material precursor from the reservoir to the microsyringe needle, and a multidirectional controller so that droplets may be brought into contact with the area between the pads. Automatic alignment of the needle tip to the dispensing location may be achieved in manufacturing, for example, using an optical recognition system using one or more fiduciary marks.

In a preferred embodiment, particularly for low-cost compatible manufacturing methods, the process of depositing the TTI material precursor may be substantially similar to the printing process that is employed for the manufacture of sensing membranes onto electrodes (see, e.g., U.S. Pat. No. 5,554,339) and the printing of reagents onto surfaces or conduit walls of cartridge components for subsequent dissolution into a blood sample.

While the present invention is conceived in a first embodiment as a process for determining device usability, in a second embodiment, the invention may be used for sensor correction. Thus, in the first embodiment, for example, the invention is to a device configured for determining device usability comprising a TTI material, e.g., a continuous polymer layer, formed on a substantially planar surface wherein the surface comprises two adjacent electrical contact pads. As indicated above, the TTI material preferably covers at least a portion of the two electrical contact pads and a portion of the space on the surface between the contact pads. In a preferred embodiment, a preselected potential or potential cycle is applied to the pads and the impedance (Z) or current (I) associated with the TTI material is measured, and the resulting measured value is compared with a predetermined threshold value to determine whether the device is usable.

In the second embodiment, the invention is to a device a sensor and a TTI material, e.g., continuous polymer layer, formed on a substantially planar surface wherein the surface comprises two adjacent electrical contact pads. The TTI material covers at least a portion of the two electrical contact pads and a portion of the space on the surface between the contact pads. In operation, a preselected potential or potential cycle is applied to the contact pads and an electrical property, e.g., impedance or current, associated with the TTI material is measured. The measured value is converted to a correction parameter that is applied to a signal from the output of the sensor to provide a corrected sensor signal.

In a related embodiment, the invention is to a method of correcting a signal in a sensing device, comprising the steps of: (a) providing a sensing device comprising a sensor, a first electrical pad, a second electrical pad, and a TTI material, e.g., continuous polymer layer, contacting at least a portion of the first and second electrical pads; (b) applying a potential across the first and second electrical pads; (c) measuring an electrical property associated with the TTI material; (d) determining a correction factor associated with the measured electrical property, e.g., from a look up table or the like; and (e) applying the correction factor to a signal generated by the sensor to produce a corrected signal.

In order to determine the appropriate correction factor, e.g., from a look up table or correction algorithm, it is necessary to establish a relationship between the electrical property and the correction factors. Thus, in another embodiment, the invention is to a method of determining a correction factor comprising the steps of: (a) providing a plurality of devices, each of said devices comprising a sensor; a first electrical pad; a second electrical pad; and a continuous polymer layer contacting at least a portion of the first and second electrical pads, wherein said devices have been exposed to different environmental conditions; (b) measuring an electrical property of the continuous polymer layer for each of the devices; (c) measuring a sensor signal for a control fluid for each of the devices; and (d) correlating the measured electrical properties with the measured sensor signals for the plurality of devices to determine the correction factor.

In a more generalized embodiment, the invention is to a device having a TTI material, e.g., continuous polymer layer, formed on a substantially planar surface, wherein the surface comprises two adjacent electrical contact pads. The TTI material covers at least a portion of the two electrical contact pads and a portion of the space on said surface between said pads. When a preselected potential or potential cycle is applied to the contact pads and an electrical property, e.g., impedance or current, associated with the TTI material is measured, the measured value determines whether the device is usable and, if the device is usable, whether it is necessary to correct the signal. If it is necessary to correct the signal, the device may determine the appropriate correction factor and modify a sensor signal from the device based on the correction factor to provide a corrected signal. For example a portion of a manufacturing lot of devices can be tested under different storage condition and tested with a standard liquid of known composition (control fluid). If the TTI value and control fluid values are recorded, any variation between the expected and measured control fluid value can be correlated with the TTI value and a correction algorithm created. This can then be implemented in the instrument when running real samples with that manufacturing lot of devices.

For both embodiments, the TTI material preferably comprises a continuous polymer layer that preferably comprises a polymer matrix, a plasticizer and a salt. Typically the continuous polymer layer comprises from 10 to 60 wt. %, e.g., from 20 to 40 wt. %, polymer matrix, from 40 to 90 wt %, e.g., from 60 to 80 wt. %, plasticizer, and from 0.05 to 20 wt. %, e.g., from 0.1 to 10 wt. %, salt. The polymer matrix optionally is selected from the group consisting of polyvinylchloride (PVC), polyurethane (PU), polyvinylacetate, carboxylated PVC, hydroxylated PVC and polydimethylsiloxane (silicon rubber). The plasticizer is optionally selected from the group consisting of trioctyl phosphate (TOP), nitrophenyloctyl ether (NPOE), bisethylhexylsebacate (BEHS), trimethyl trimellitate (TMTT), dioctyl adipate (DOA) and diisobutyl phthalate (DIBP). The salt is preferably highly lipophilic so as to enhance polymer solubility and can be either organic or inorganic. Exemplary organic salts may be selected from the group consisting of dodecyl sulfosuccinate, lauryl sulfate, alkyl ether phosphates, tetramethylammonium salts, benzalkonium salts, cetylpyridinium salts and zwitterionic organic salts, e.g., cocamidopropyl hydroxysultaine. Exemplary inorganic salts may be selected from the group consisting of iodide, bromide, perchlorate and zwitterionic inorganic salts. In a preferred embodiment the salt comprises quaternary ammonium borate.

The specific composition of the TTI material precursor, e.g., polymer layer precursor, that is used to form the TTI material, e.g., continuous polymer layer, may vary widely. In an exemplary embodiment, the TTI material precursor comprises a polymer, the plasticizer, and the salt, as discussed above, but preferably further comprises a carrier medium (e.g., solvent) for imparting the desired physical properties for deposition thereof as well as solubilizing the polymer contained therein. In another embodiment, the precursor comprises a monomer and an initiator, and polymerization may occur after deposition of the TTI material precursor onto the surface, e.g., through free radical polymerization, optionally with application of UV radiation.

The carrier medium may comprise water or an organic solvent. As these materials are preferably microdispensed onto the contact pads using microdispensing methods and equipment as described in jointly owned U.S. Pat. No. 5,554,339 previously incorporated herein by reference, similar considerations as to ingredients, viscosity, surface preparation and pretreatment and the like also apply to the present invention.

As described above, the continuous polymer layer is preferably formed by microdispensing one or more drops of the precursor onto the substantially surface and removing the carrier medium, optionally with heat, and/or drying the precursor to form the TTI material. In a preferred embodiment, e.g., for the embodiments described in the examples below, the deposited precursor forms a substantially circular shape having a diameter in the range of from about 20 µm to about 2 mm, preferably 100 µm to 500 µm, and is generally domed, covering the distance between the two pads, which preferably is in the range of from about 10 µm to 1 mm, preferably from about 10 µm to 200 µm. The average thickness of the layer is generally in the range of from about 1 µm to about 200 µm, preferably from about 20 µm to about 60 µm. One skilled in the art will appreciate that ranges outside of those provided above may be employed, for example, for larger sensor devices such as some home use glucose testing strips.

Various potential cycles may be used in measuring the electrical property associated with the TTI material, e.g., continuous polymer layer. In some exemplary embodiments, the potential cycle may be selected from a sigmoidal potential cycle, a fixed applied potential, and a potential that is a sequence of fixed applied potential steps. Measurements may be made, for example, with an impedance measuring circuit in an instrument, or a current measuring circuit in an instrument. In a preferred embodiment, an initial current value associated with the TTI layer is measured when the device is manufactured and the threshold level is at least three times, preferably at least five times, lower than the initial current value. Conversely, in another aspect, an initial impedance value associated with the TTI material is measured when the device is manufactured and the threshold level is at least three times greater, preferably at least five times greater, than the initial impedance. In some exemplary embodiments where current is measured, the current ranges from picoamps to milliamps, but more typically from nanoamps to microamps, e.g., from 0.1 to 100 nanoamps. Where impedance is measure, the typical impedance may range, for example, from below the megaohm range to above the gigaohm range, more typically in the tens of megaohms to low gigaohm range, optionally from 100 to 1500 megaohms at a frequency of from about 1 to about 10 Hz.

Where a sensor correction is made, the correction value may be selected from an amperometric correction value, a potentiometric correction value, a coulombic correction value and a conductivity correction value. These values are typically applied to a sensor selected from the group consisting of a pH sensor, oxygen sensor, carbon dioxide sensor, hematocrit sensor, glucose sensor, lactate sensor, creatinine sensor, sodium sensor, potassium sensor, magnesium sensor, calcium sensor, chloride sensor, phosphate sensor, liver enzyme sensor, BNP sensor, troponin sensor, BUN sensor, CKMB sensor, NGAL sensor, TSH sensor, D-dimer sensor, PSA sensor, PTH sensor, cholesterol sensor, ALT sensor, AST sensor, prothrombin sensor, APTT sensor, ACT sensor, galectin sensor, and combinations thereof.

One desirable feature of the present invention is that it may be easily adaptable to widely available commercial technologies and can be performed with existing electronics that require no hardware changes but only a software modification, which are generally simpler to implement than hardware modifications. For example, an i-STAT instrument may be able to measure conductivity at 10 kHz and 50 kHz, but may be conveniently expanded to a wider frequency range. In a preferred embodiment, this circuitry is programmed to measure the electrical resistance between adjacent contact pads at a frequency of 10 Hz. It has been found that low frequency impedance measurements in the range of from about 1 Hz to about 100 Hz are most sensitive in detecting a change in the electrical property of the TTI material. Without being bound by theory, it is understood that changes in circuit impedance may be due to a change in the bulk membrane resistance, which is best observed when the ions in the membrane migrate some distance so they must be under a polarizing voltage for some time, which requires a low frequency. One possible mechanism is that at higher frequencies, the voltage oscillates so quickly that the ions do not migrate appreciably. As a result, the resistance to their movement does not influence the impedance. Another possibility is that the impedance change over time that is observed in the present invention may be contributed in part by the electrode oxidation and its interface with the bulk polymer membrane. In general, electrode polarization impedance becomes more significant at lower frequencies than at higher frequencies. In any event, an important parameter to the present invention is an empirically observable and consistently predictable change in the electrical property.

To avoid compromising the use of the contact pads for their primary function, typically analyte sensing, where the electrical property that is measured is the open circuit resistance, the $R_{TTI}$ preferably is much greater than, e.g., at least 1000 times greater than, the closed circuit resistance, i.e., the resistance measured between the electrodes attached to the contact pads with either sample or calibrant fluid covering the electrodes. However, the $R_{TTI}$ preferably is much lower, e.g., at least 100 times lower, than the existing open circuit resistance, i.e., the resistance between the contact pins prior to contacting the pads. This goal may be accomplished through careful design of the geometry of the TTI material and control of the TTI composition. Thus, a reduced cross-sectional polymer layer area and an extended polymer pathlength between the pads will generally lead to an increased resistance for any given material composition, whereas increasing the ionic content and ion mobility of the polymer layer for a given geometry will generally lead to a decreased resistance. Note that the typical sample or calibrant fluid resistance is in the range of about ten to thousands of ohms, whereas the open circuit resistance is generally greater than several giga-ohms. Thus, the TTI resistance is preferably in the mega-ohm to low giga-ohm range, as shown in the appended figures.

One important feature of the present invention is establishing a quantitative relationship between $R_{TTI}$ and actual aging of a test cartridge. As indicated above, the objective is to prevent expired cartridges from being used and prevent usable cartridges from being discarded. Thus, in another embodiment, the invention is to a method of determining a threshold level associated with analytical device usability. The method comprises the steps of: (a) providing a plurality of devices, each of said devices comprising a sensor; a first electrical pad; a second electrical pad; and a continuous polymer layer contacting at least a portion of the first and second electrical pads, wherein said devices have been exposed to different environmental conditions; (b) measuring an electrical property of the continuous polymer layer for each of the devices; (c) measuring a sensor signal for a control fluid for each of the devices; (d) identifying a subset of said plurality of devices that provide a signal having a predetermined acceptable precision level for said control fluid; and (e) determining the threshold level that corresponds to the electrical property of the continuous polymer layer for the subset of said plurality of devices.

The present invention advantageously avoids the need to add to the TTI material conductive particles, e.g., carbon black, conductive carbon nanotubes, metallic particles, metallic oxide, semi-conductor particles, to adjust the initial resistivity to the desired level. By contrast, the present invention, in some aspects, relies on a TTI material comprising a polymer, i.e., a non-conductive material, and various other molecular species. While these species may be polar or ionic and thus affect the conductivity of the TTI material, they are not particulate in nature. In the preferred embodiment, lipophilic organic ammonium ion salts are used, e.g., dodecylammonium chloride and tetraphenylborate to impart the desired degree of resistivity/conductivity. Nevertheless, in other aspects of the invention, such conductive particles may be included in the TTI material precursor as well as the TTI material used in the devices and methods of the invention.

The TTI material should be accurately positioned in the devices in order, for example, to avoid potential contamination of the connector, e.g., connector pins, in the instrument. Notably, the transfer of polymeric material from the TTI material to the connector pins should be minimized or avoided. Consequently, in some aspects, the present invention also relates to devices having a boundary structure that facilitates controlling the spreading of the dispensed precursor that forms the TTI material, e.g., continuous polymer layer. The boundary structure may, for example, be positioned at a predetermined region of the device, for example as a polygon, e.g., square, pentagon, hexagon, octagon, and the like, or as a cylindrical or ring shape. This boundary structure, if employed, preferably is positioned in a manner that intersects the two adjacent pads.

In embodiments where the connector pin tips initially contact the top portion of a pad and move slightly towards the middle of the chip as the connector applies more force, it is preferred that the boundary structure, e.g., ring, locations closer to the middle of the chip are used for locating the polymer layer. In this manner, the TTI material preferably is positioned beyond the extent of travel of the pin tip, thus obviating the contamination issue. The scratch marks in the middle of the contact pads in FIG. 1B, discussed below, show where the connector pins have hit the contact pads and moved during connector engagement. An exemplary boundary structure is discussed in the following Examples.

EXAMPLES

Figure 1B:
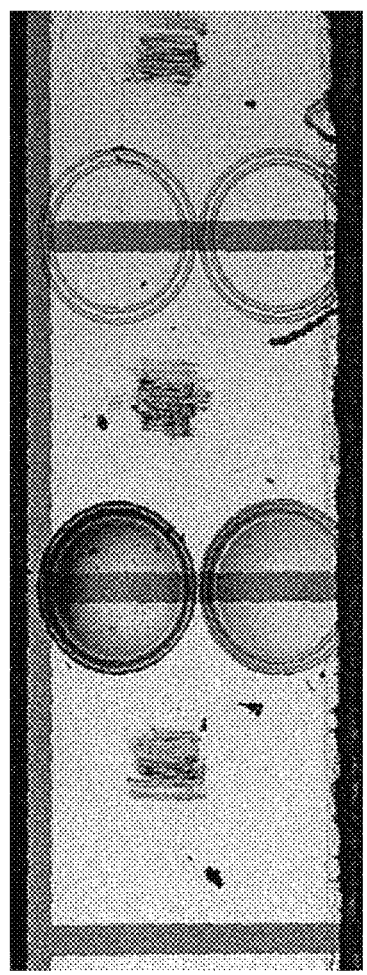

Six TTI material formulations were tested on silicon chips of the type shown in FIGS. 1A and 1B. The silicon chips were made on wafers according to the general processes as described in jointly owned U.S. Pat. Nos. 5,200,051 and 7,419,821. Six contact pads are shown at the top of the chip, two of which are each connected to a round amperometric sensor by a conducting line, and two are connected to parallel hematocrit sensing bars. Six circles indicate the locations for printing the TTI material. The overall dimensions of the chip are about 3×5 mm and the TTI material diameter is about 0.2 mm FIG. 1B is an image of an actual chip with two rings printed with TTI material (left) and two rings without TTI material (right). Four optional positions for boundary structures are shown. Note the domed shape of the printed structure is apparent in FIG. 1B. The boundary structure may be formed, for example, by patterning a ridge of passivation material, e.g., a photoformable polyimide. Note that a photoformable passivation material may be spin-coated and patterned to form an insulating layer over the contact lines on the chip in FIGS. 1A and 1B. Thus, the mask for that process may also include the ring structures as shown. Jointly owned U.S. Pat. No. 5,200,051, the entirety of which is incorporated by reference, discloses similar processes. Other photoformable materials, e.g., those based on polyvinyl alcohol or dichromated gelatin, may also be used.

FIG. 2 presents two tables with the different TTI material precursor formulations that were prepared and evaluated. Different solids content of ETH-500 (Tetradodecylammonium tetrakis(4-chlorophenyl) borate) and ratios of TOP, NPOE, BEHS and PVC with high and low molecular weight PVC materials were investigated as shown in formulations 1-6 and A-C. These formulations were printed using the microdispensing method described in jointly owned U.S. Pat. No. 5,554,339 onto one or more of the circled locations indicated in FIG. 1.

Chips and cartridges were stored in a set of incubators from 5° C. to 50° C. at a controlled humidity, with the initial time recorded. They were tested within about 20 minutes of removal. The temperatures indicated in the figures indicate the actual storage temperature. Note that room temperature was 25° C. in these experiments.

Figure 3A:
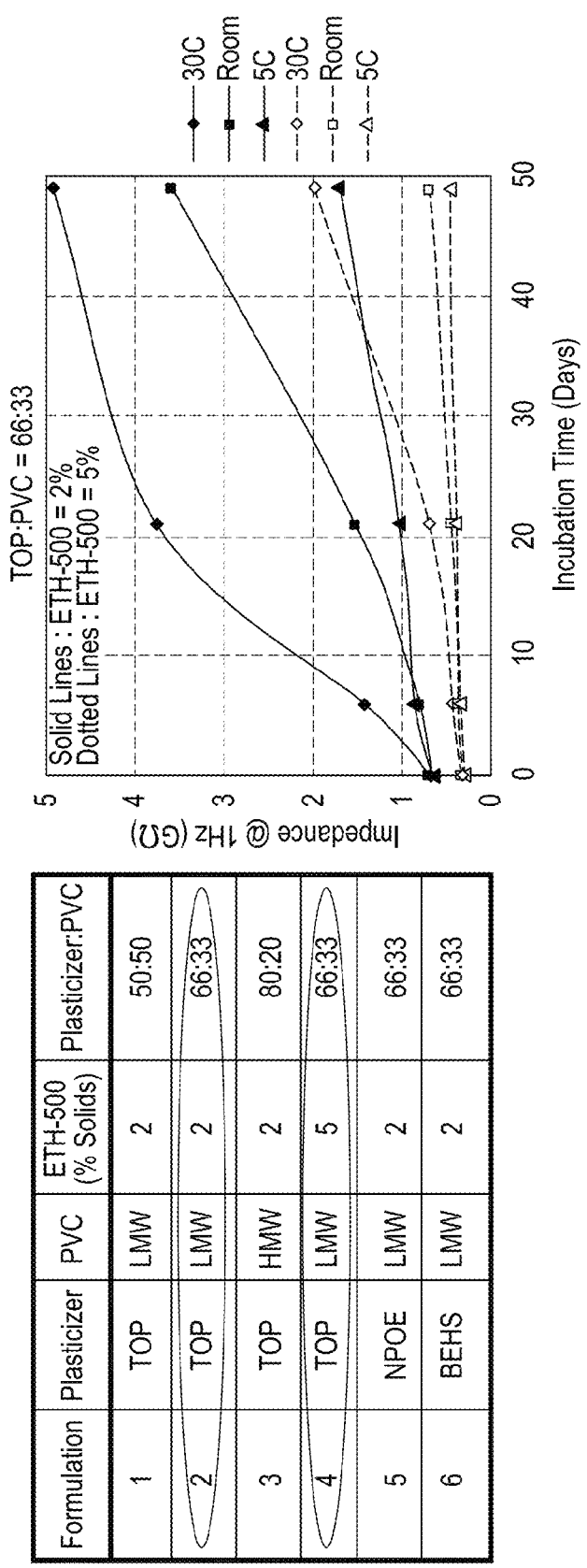
FIG. 3A and FIG. 3B show preliminary results for the indicator layers with impedance changes for different compositions at different temperatures.

Individual chips were then stored at one of four temperatures, specifically at 5° C., 13° C., 25° C. and 35° C., and tested at 0, 3, 7 and 11 weeks. The impedance of all samples except for those with NPOE increased over time, and the rate of change was greater at higher ambient temperature than at a lower temperature. As an example, FIG. 3A shows the results of formulations 2 and 4, which indicates that ETH-500 content affects the slope of the response. Comparing formulations 2 and 6 revealed that BEHS can affect the temperature coefficient of the slope, and comparing formulations 1, 2 and 3 revealed that increasing the TOP concentration mainly affects the slope (data not shown). NPOE-containing formulations generally had too high a resistance for optimum performance as a TTI material.

Figure 3B:
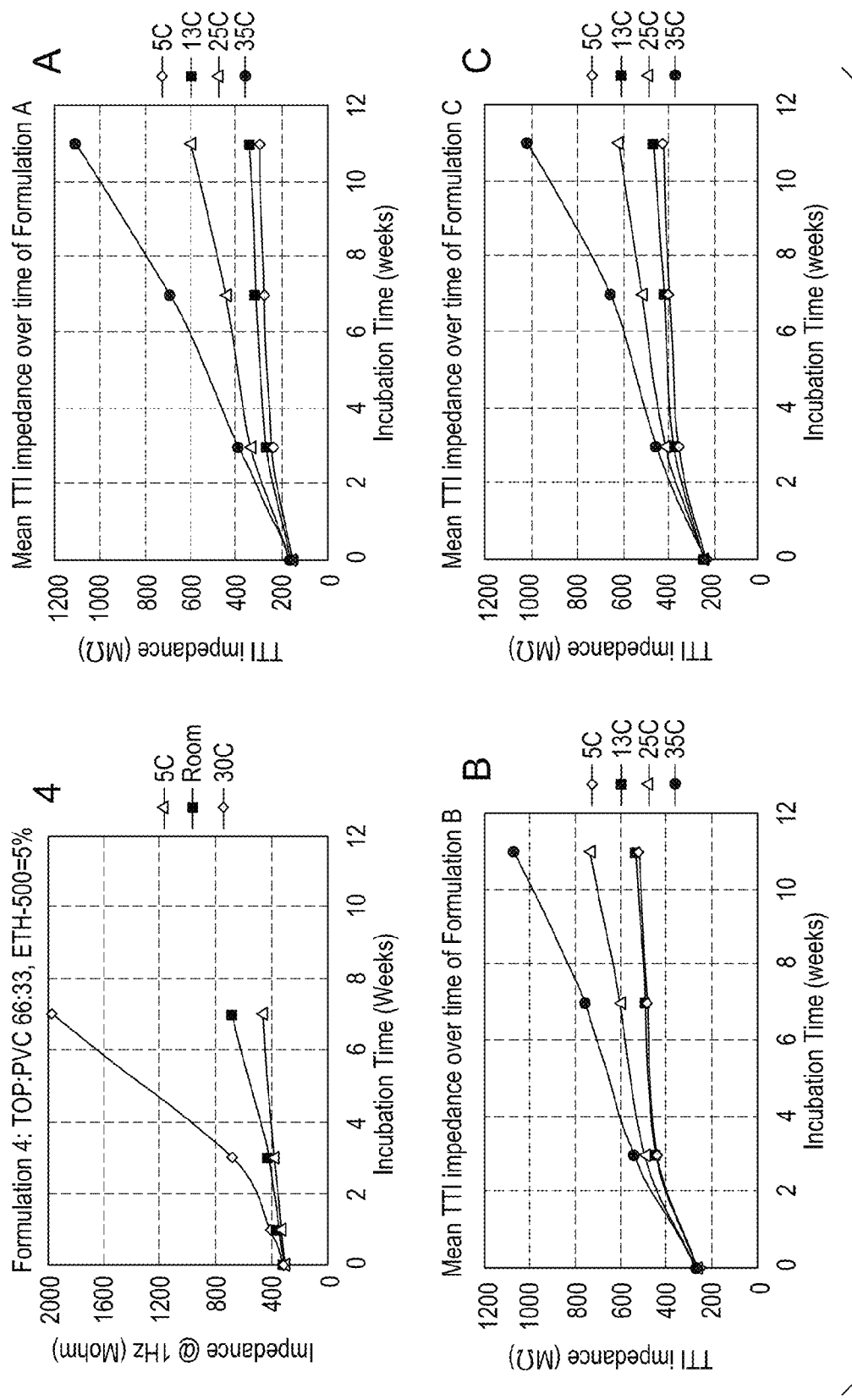

The plots in FIG. 3B show that for formulation (A), the impedance increased from an initial value of about 160 Megaohms over time, and the increase was greater with increasing storage temperature. Similar results were shown for formulations (B) and (C). For comparison, the results of formulation 4 (FIG. 2) are also plotted in FIG. 3B.

Figure 4A:
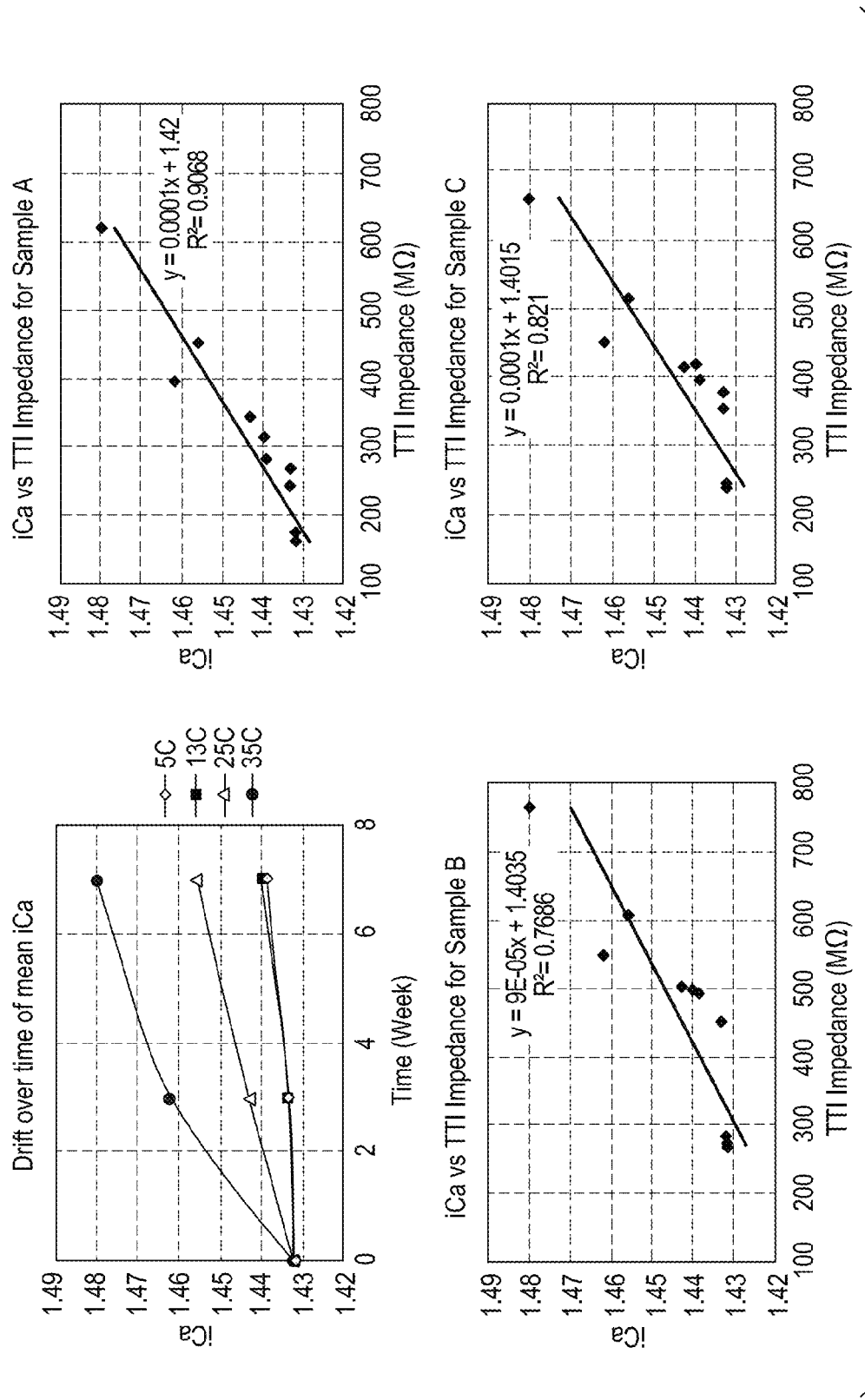
FIG. 4A shows a correlation plot for the indicator layers.

The first plot in FIG. 4A shows the mean calibrant ionized calcium value (iCa) for a set of calcium sensors as a function of time at these different storage conditions (5° C., 13° C., 25° C. and 35° C.). The three other plots in the same figure show a correlation of the iCa value with the impedance of the associated TTI material for each of the three formulations A-C. The data clearly show that the correlation can be used to set a threshold impedance value, e.g., 500 Mega-ohms, above which the iCa sensor is considered to have exceeded its shelf life and therefore should not be reported, i.e., used to determine a patient test value.

Figure 4B:
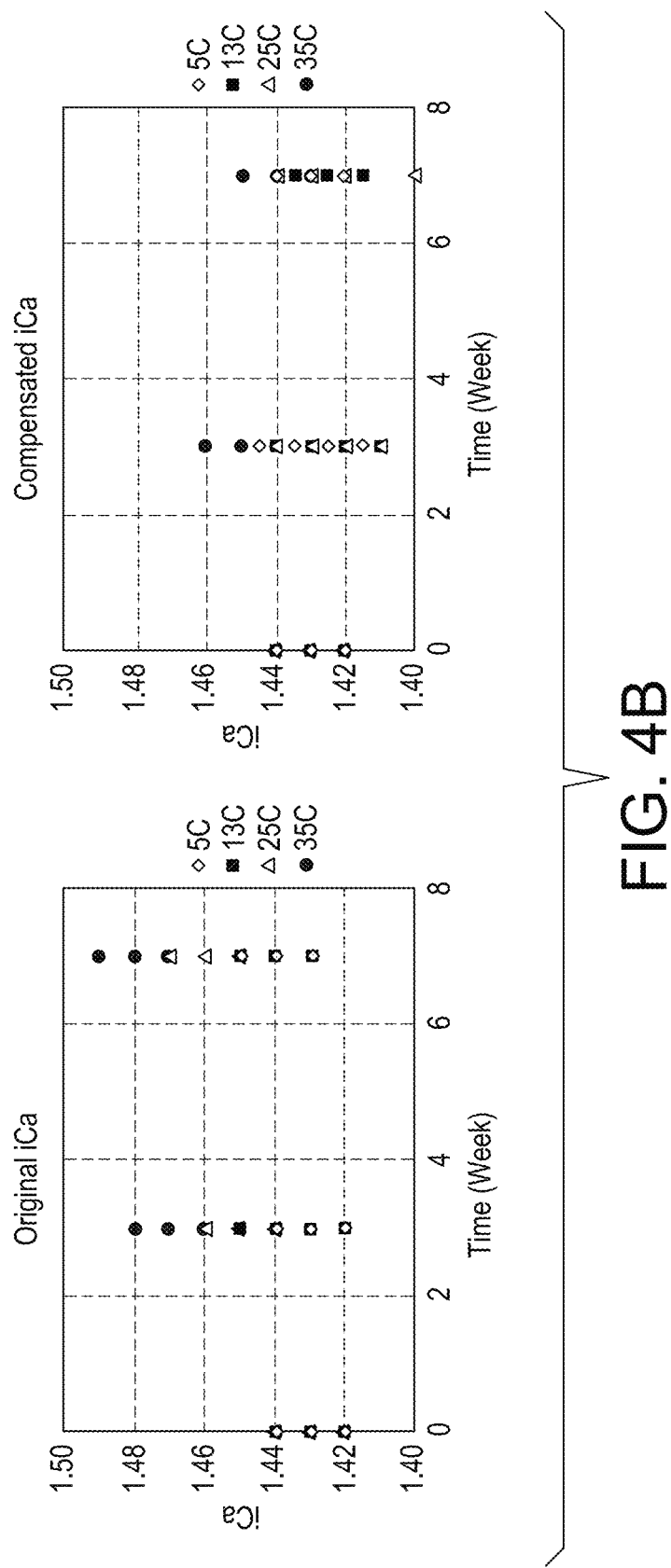
FIG. 4B shows a compensated ionized calcium test.

FIG. 4B shows the original iCa data points (left) and after correction (right) using the regression formula derived from formulation A as shown in the top-right plot of FIG. 4A. This embodiment has the advantage that it enables a sensor that would otherwise have been considered to have exceeded its shelf life to still be used based on a time and temperature integrated correction factor. Once the TTI relationship between thermal exposure and change in impedance has been established, a dynamic correction algorithm can be created and embedded into the instrument software.

Figure 4C:
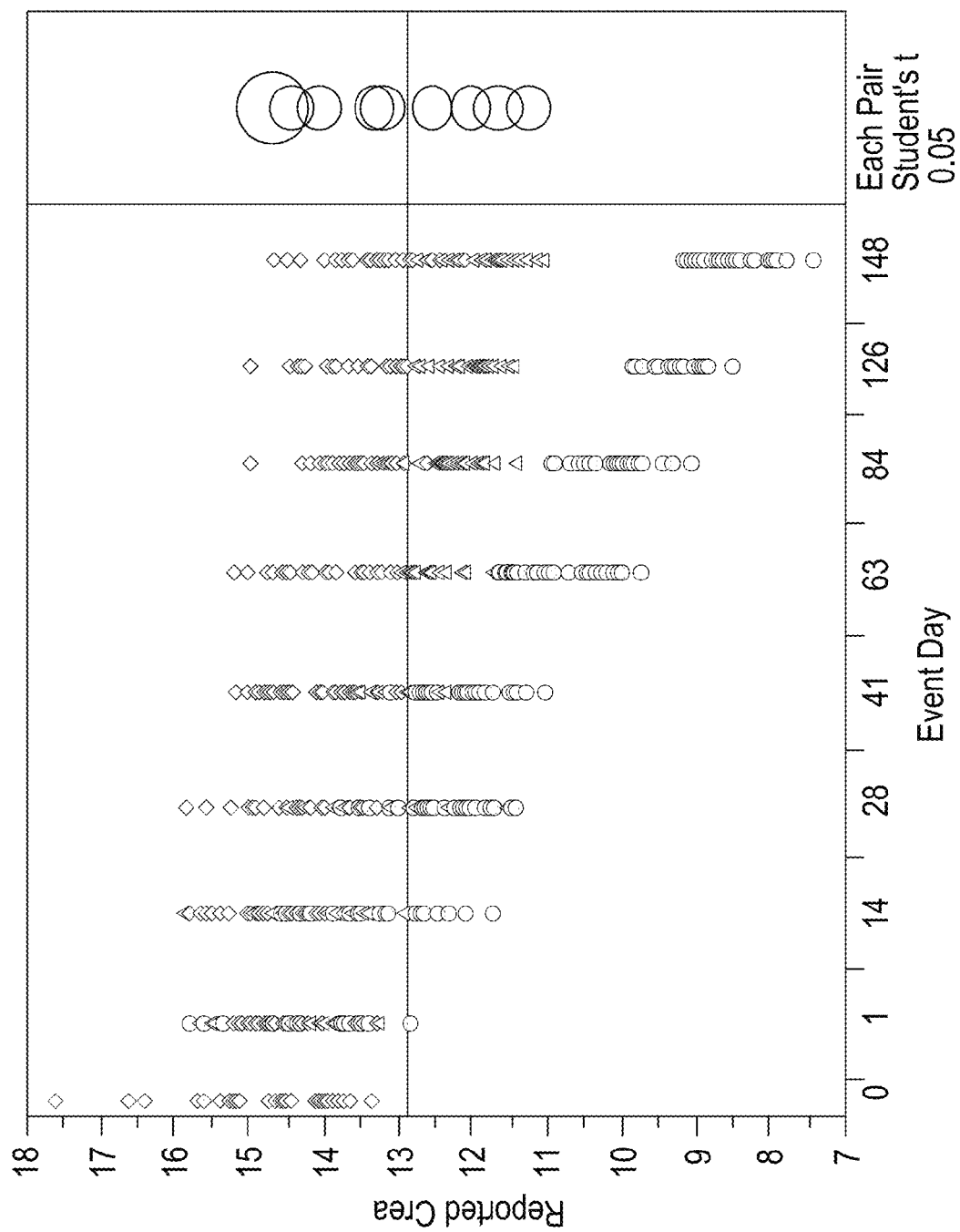
FIGS. 4C and 4D show a creatinine test before and after correction, respectively.
Figure 4D:
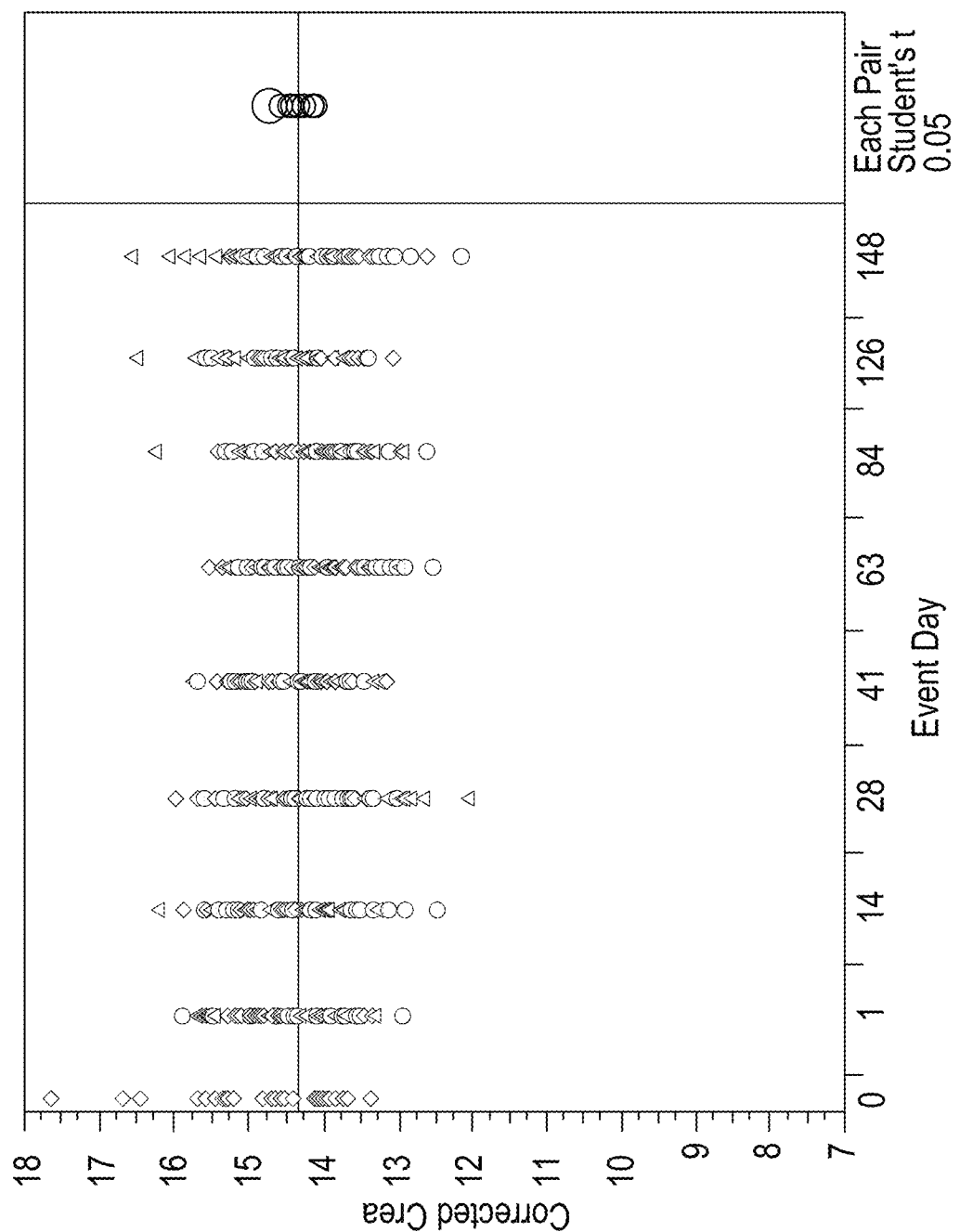

An approach to correcting an assay result for aging relies upon the following. The assay and TTI need to predictably change when subjected to the same thermal stress independent of the conditions to which it has been subjected. For example, an assay storage condition with highly fluctuating temperature (bounded by the allowable extremes) should produce nearly the same change as is observed when the assay is stored at a fixed temperature. If this condition is met, and if the time and mean kinetic temperature (MKT), which is the equivalent fixed temperature at which an assay would need to be held to reach the same degree of aging, are known then the assay result can be corrected. If the duration of thermal stress is known (ideally the time since the date of manufacturer), the TTI can be used to calculate the MKT. Based upon the relationship established between the MKT and the change in the assay result the expected change can be back calculated from the result. The correction algorithm may be derived using an Arrhenius model. An example is shown in FIGS. 4C and 4D, before and after correction, respectively, for a creatinine sensor (Crea). For example, a correction factor for creatinine may be determined by the following formula:

$$[Crea] = b * response - c$$

wherein:
"response" is the slope of the sensor response (e.g., current) for the sample;
(b) is a calibration parameter for slope (b) of the sensor response;
(c) is a calibration parameter for intercept (c).

With aging, the response slope b is changing according to Arrhenius model and creatinine concentration can be corrected as follows:

$$[CREA] = \underbrace{\frac{b}{\theta_1 \cdot \exp\left(-\left(\theta_2 \cdot \exp\left(-\frac{Ea_{CREA}}{R} \cdot \left(\frac{1}{MKT} - \frac{1}{T_{ref}}\right)\right)\right) \cdot \text{time}\right) + \theta_3}}_{c} \times \text{Response} +$$

wherein:

MKT is the mean kinetic temperature and can be estimated from the measured TTI impedance $R_{TTI}$;

$Ea_{CREA}$ is apparent activation energy for change in creatinine sensor response;

R is the universal gas constant;

$T_{ref}$ is the experimental reference temperature;

$\theta_1$ is a pre-exponential factor for time/temperature changes in b;

$\theta_2$ is the rate of change in b at $T_{ref}$; and $\theta_3$ is non-temperature dependent offset=1−$\theta_1$.

Figure 5:
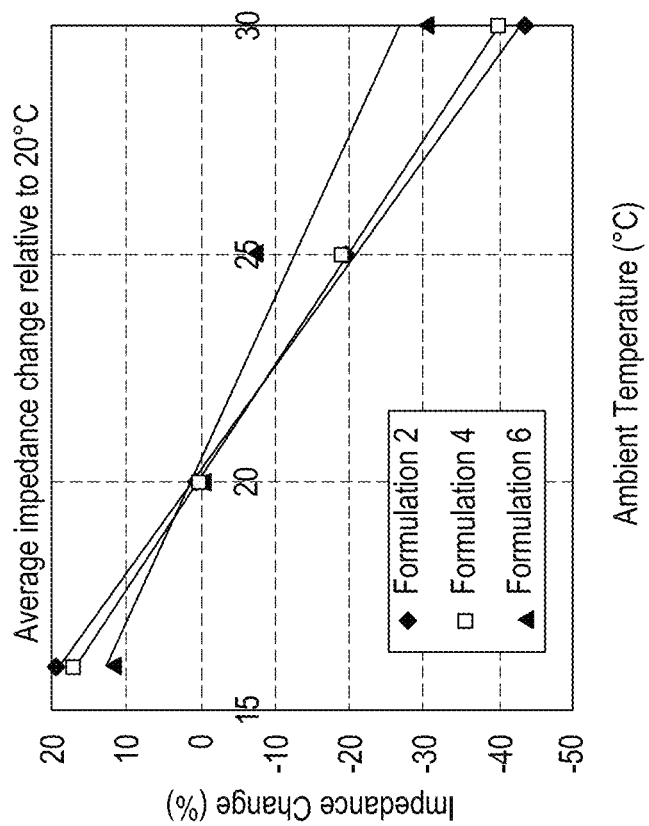
FIG. 5 shows the effect of ambient temperature on impedance.

FIG. 5 shows the effect of ambient temperature on the measurements. Impedance at a frequency of 1 Hz was measured for formulations 2, 4 (data shown at week 7) and 6, and for each formulation 5 devices were tested at 16° C., 20° C., 25° C. and 30° C., respectively. Correlating data for formulations 2, 4 and 6 in the second graph shows that the impedance decreases with temperature at ~3-4%/C. Due to the significant temperature dependence on impedance, an ambient temperature measurement would be needed to correct the measured impedance to the standard reference temperature, e.g., standard room temperature of 23° C. Otherwise, the TTI device should be measured at a fixed temperature, e.g., 37° C. standard body temperature, although this would reduce the sensitivity (ΔZ/Δtime-temp) of the TTI device.

Figure 6:
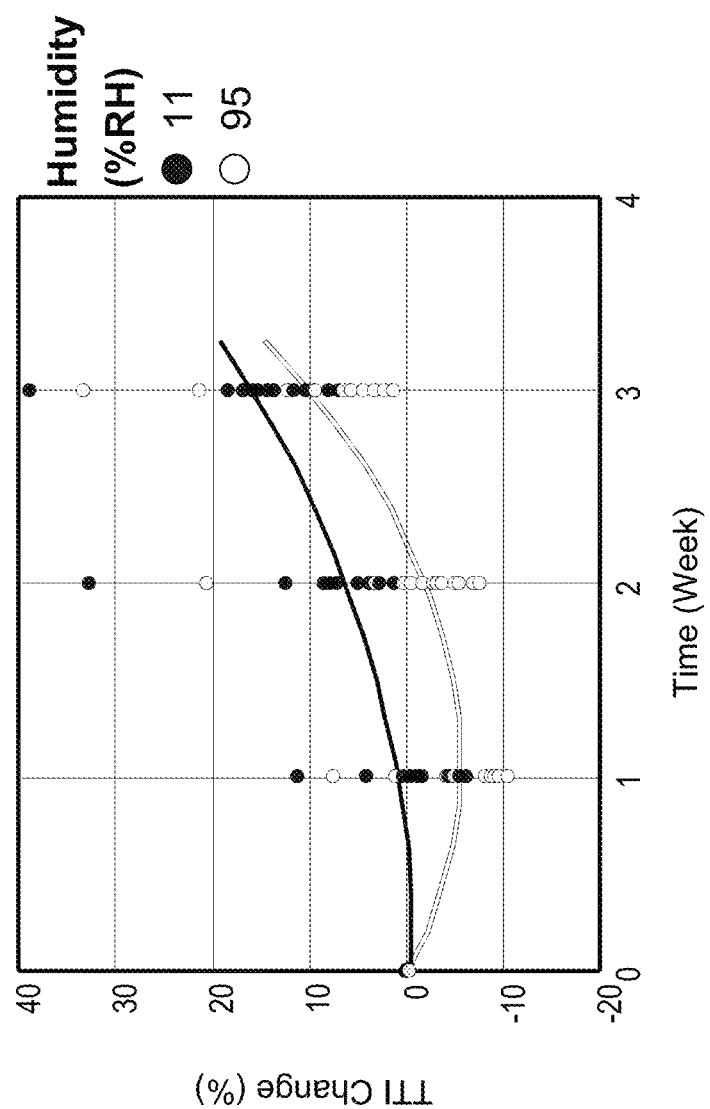
FIG. 6 shows the effect of storage humidity on impedance.
Figure 7:
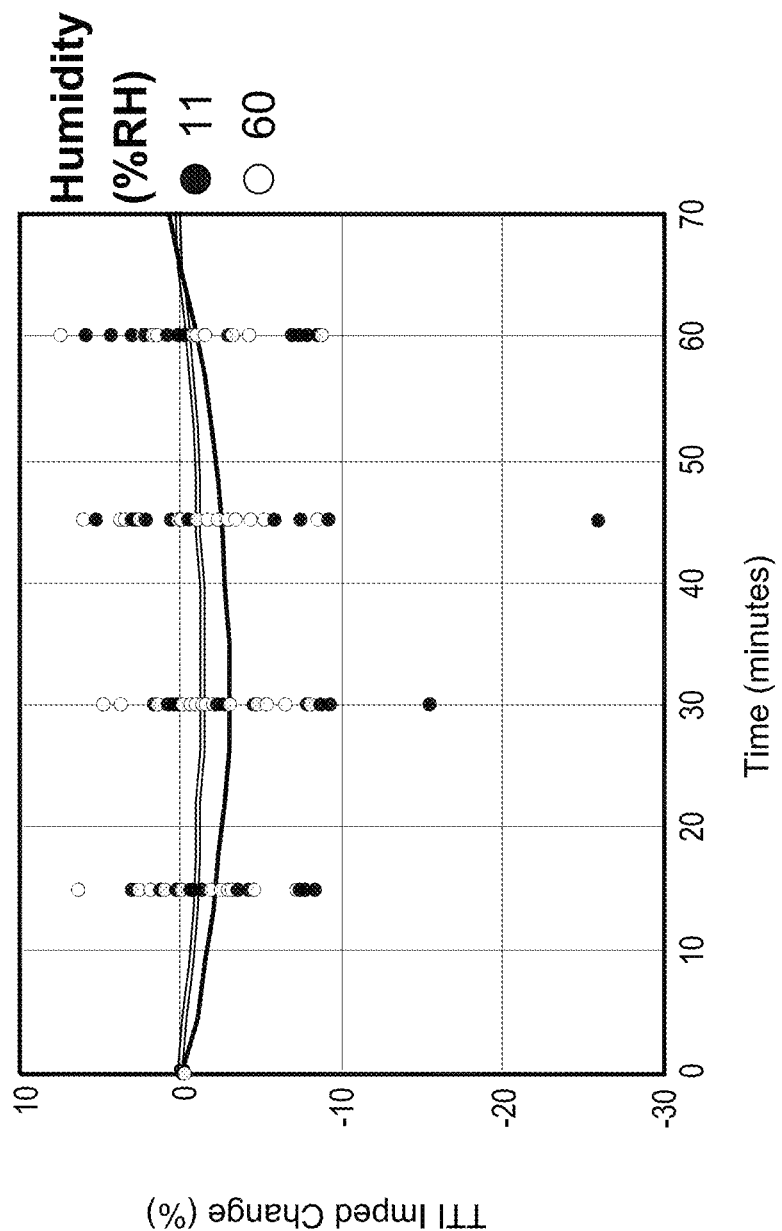
FIG. 7 shows the effect of ambient or operational humidity on impedance.

The effect of storage and operational humidity were also studied. Formulations A, B and C were tested with devices stored at 11% and 55% relative humidity (RH). FIG. 6 shows a plot of impedance amplitude (Zmod) versus time and shows that the effect on storage was small. Therefore, humidity did not appear to be a significant variable in the TTI material design. FIG. 7 shows similar data for the same formulations during operation, i.e., simulation of the actual cartridge test cycle, at 11% and 95% RH. Again, the results indicated that operational humidity was not a significant variable in TTI design.

Figure 8B:
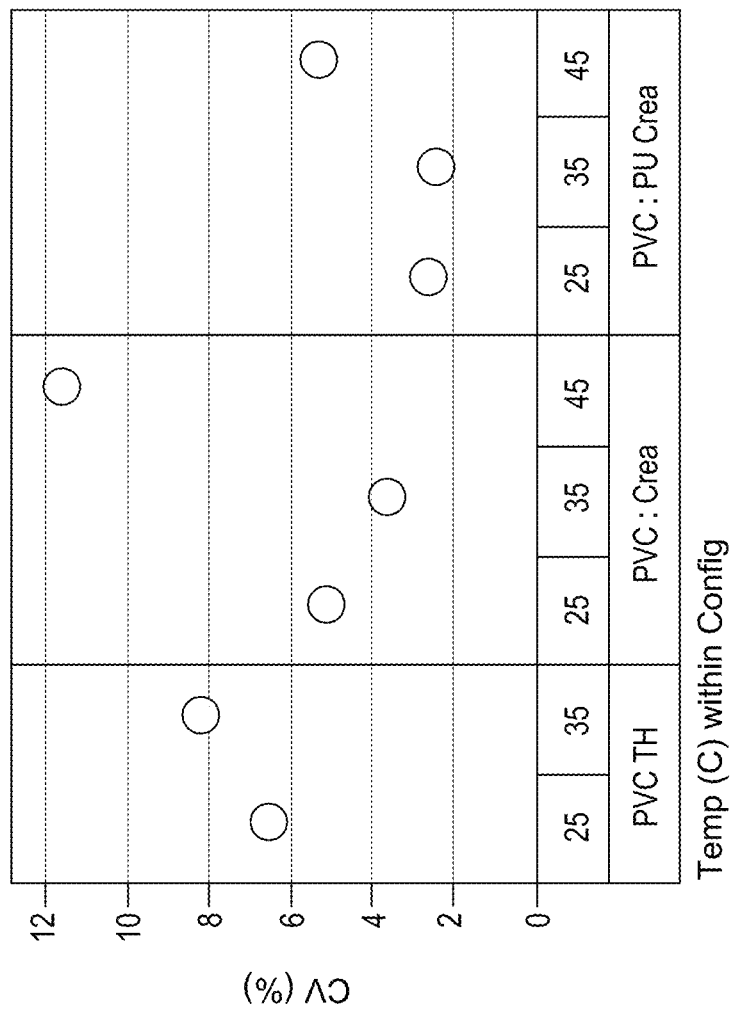
FIG. 8 shows impedance variability with time.

FIG. 8A shows that the variability of the results of formulation A printed on an immunosensor chip (of the type shown in FIG. 1) aged at 35° C. became greater over time. It was also noticed that the variability increased with increasing temperature. Without being bound by theory, there is a possibility that the increased variability is caused by separation of the polymer material from the metal contact pads. This delamination would cause a smaller cross sectional contact area between the polymer and electrode, thereby increasing resistance. Ensuring that the TTI material does not delaminate from the contact pads (and the dielectric substrate) is important in ensuring multiple mechanisms are not influencing the measured impedance. FIG. 8B compares the variabilities of 3 configurations (PVC on TH chip, PVC on Crea Chip, and PVC+PU on Crea Chip) after being aged at 25° C., 35° C. and 45° C. for about 17 days. The results indicated that the last configuration improved the repeatability significantly (down to <3% CV at 25 C and 35 C).

Figure 9:
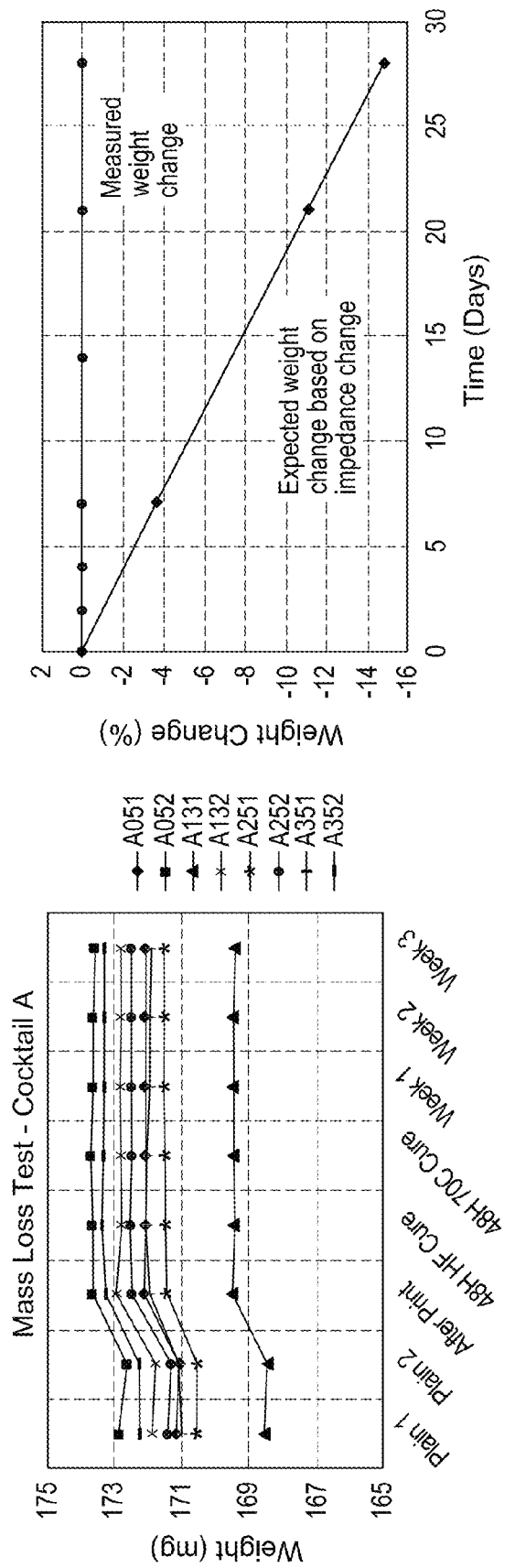
FIG. 9 presents data from a plasticizer loss study.

One of the basic questions in the present study was seeking to identify the cause or causes of the impedance change. One potential source was mass loss of the more volatile components of the polymer layer mixture. FIG. 9 shows the data for formulation A where continuous polymer layers were printed onto glass slides and weighed before and after printing and during storage at 5° C., 13° C., 25° C. and 35° C. In FIG. 9, Plain 1 and 2 refer to the slide before printing. In the period immediately after printing and after the performance of various curing steps and also after storage for three weeks, it was found that the measured mass did not change significantly. Formulation B material was also printed and tested in the same way with similar results.

Without being bound by theory, the mechanism for increasing impedance of the TTI material appears to be a subtle combination of at least some of the following variables: plasticizer evaporation, chemical changes, component degradation, changes in the mobility of the electrolyte components, polymer reorganization between amorphous and crystalline states, salt precipitation, phase separation, interfacial changes between the electrode surface and the polymer layer, partial delamination and polymer creep. With respect to the present invention however, repeatable empirical observation of a consistent and predictable rate of change is the basis of utility of a practical device.

Figure 10:
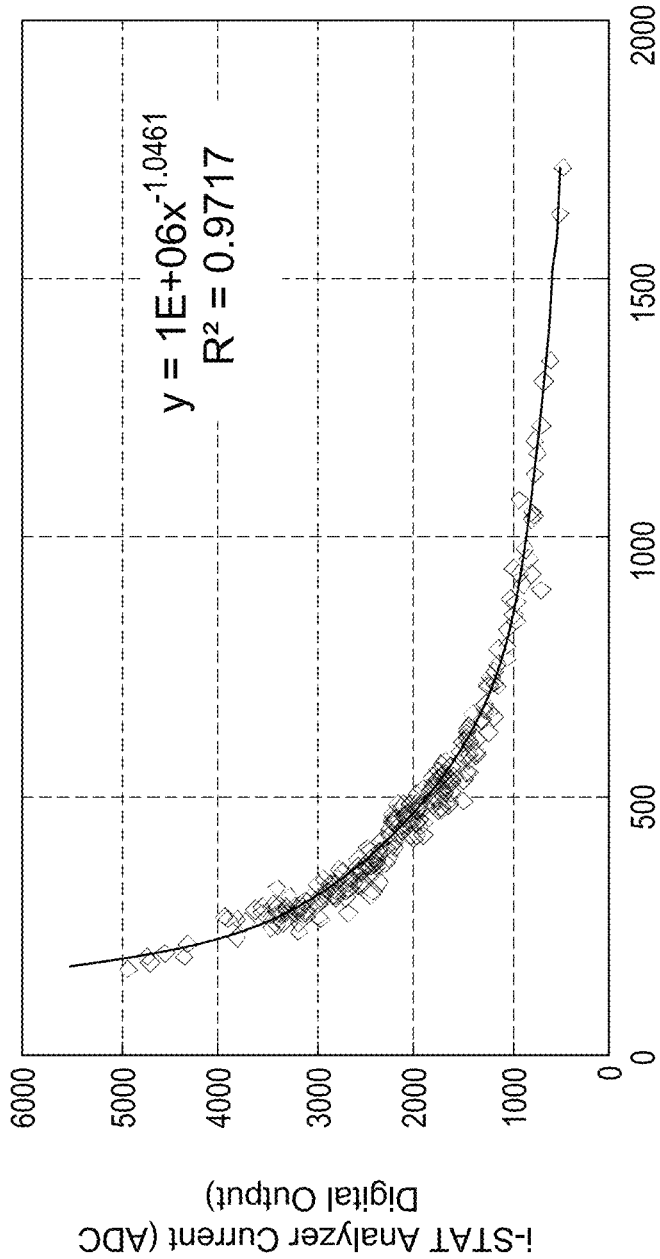
FIG. 10 shows the impedance measurement correlation for different test systems.

With regard to practical implementation of the present invention, FIG. 10 shows the correlation of data for formulations A, B and C tested using standard analytical equipment for measuring impedance (Gamry Reference 600, Gamry Instruments, 734 Louis Drive, Warminster, Pa. 18974) compared to the analog to digital converter (ADC) output of the hematocrit channel of an i-STAT1 instrument. About 270 cartridges were aged at various temperatures and tested. The figure shows a reasonably tight relationship between the two measurement protocols indicating that the commercially established i-STAT1 circuitry was suitable for measuring a TTI without modification beyond the appropriate software changes. Based on the curves shown in FIG. 10, the threshold values for determining if a particular cartridge has exceeded its useful life due to age and/or temperature exposure can be assigned for a given TTI material precursor formulation. Likewise, a sensor correction factor can also be assigned.

By utilizing the present invention it is possible to significantly further extend the time available for typical room temperature storage of blood testing devices. In this context, the improvement can be at least about 50%. In addition, the invention may be applied to any electrochemical test device where the instrumentation enables current or impedance measurements, e.g., glucose meters used for diabetes monitoring with electrochemical sensor strips. The invention also simplifies the process of implementing point of care testing technology for the user, e.g., nurse, doctor or other healthcare professional. It also ensures that test devices, e.g., cartridges, strips and the like, have been stored properly prior to the use of each individual device. It can be used to compensate for device aging factors and improve the accuracy of results throughout the life of the device.

In another embodiment of the present invention, the measured value from the TTI is used to calculate the remaining percentage of thermal stress for the rest of a manufacturing lot of the same devices stored under the same conditions. This is essentially the length of time for room temperature storage that remains for all of the other devices that were stored with the tested device but have yet to be used. As all of the devices in a given lot (e.g., a given i-STAT cartridge manufacturing lot) are manufactured in the same way and at the same time, the tested device gives a measured impedance or current value that not only is relevant to that particular device (as applied in other disclosed embodiments) but can also be used predictively with respect to other devices from the same manufactured lot that have been subjected to the same storage conditions as the tested device.

For example, assuming a thermal stress budget of 100% at the time the lot of cartridges are removed from refrigeration, at the time a particular cartridge is tested, it is possible to calculate from the measured TTI value that some fraction of the budget remains, i.e., a value from 100% to 0% (expiry). This is based on an embedded data curve reflecting this range that is part of the instrument software algorithm. The curve is derived from the type of data shown in the various figures, i.e., factory determined and uploaded to the instrument for predetermined lots.

Optionally, this information is displayed on the instrument and relayed to the hospital's point of care coordinator. This enables a new supply of devices, e.g., a new box of cartridges, to be ordered when expiry is imminent. It also enables the creation of a cartridge management report that allows the point of care coordinator to easily monitor and manage cartridges throughout a facility in a remote manner. Note that in practice, individual cartridges are generally traceable to a particular box and it is a reasonable assumption that cartridges are stored together in the box. Consequently, every time a cartridge is run from a particular box it provides useable information on the amount of room temperature storage for the remaining cartridges in that box and all boxes stored similarly.

While the invention has been described in terms of various preferred embodiments, those skilled in the art will recognize that various modifications, substitutions, omissions and changes can be made without departing from the spirit of the present invention. Accordingly, it is intended that the scope of the present invention be limited solely by the scope of the following claims.

What is claimed is:

1. A method of determining device usability, comprising the steps of:
    providing a device comprising a first electrical pad; a second electrical pad; and a continuous polymer layer contacting at least a portion of the first and second electrical pads;
    applying, by an instrument, a potential across the first and second electrical pads;
    measuring, by the instrument, an electrical property associated with the continuous polymer layer;
    determining, by the instrument, whether the measured electrical property associated with the continuous polymer layer has exceeded a threshold level associated with the device usability; and
    determining, by the instrument, the device is valid for use when the measured electrical property associated with the continuous polymer layer does not exceed the threshold level,
    wherein the continuous polymer layer comprises a polymer matrix, a plasticizer and an organic salt, and
    wherein the continuous polymer layer comprises from 20 to 40 wt.% polymer matrix.

2. The method of claim 1, wherein the polymer matrix comprises a polymer selected from the group consisting of polyvinyl chloride (PVC), polyurethane, polyvinylacetate, carboxylated PVC, hydroxylated PVC and polydimethyl siloxane.

3. The method of claim 1, wherein the continuous polymer layer comprises from 60 to 80% plasticizer.

4. The method of claim 1, wherein the plasticizer is selected from the group consisting of trioctyl phosphate (TOP), nitrophenyloctyl ether (NPOE), bisethylhexylsebacate (BEHS), trimethyl trimellitate (TMTT), dioctyl adipate (DOA) and diisobutyl phthalate (DIBP).

5. The method of claim 1, wherein the electrical property comprises current, resistance, impedance, conductivity, or a combination thereof.

6. The method of claim 1, wherein the distance between the first and second electrical pads is from 10 µm to 2 mm.

7. The method of claim 1, wherein the potential comprises a sigmoidal potential cycle, a fixed applied potential, a sequence of fixed applied potential steps, or a combination thereof.

8. The method of claim 1, wherein the potential comprises a potential cycle that is applied at a predetermined frequency in the range of about 1 Hz to about 100 Hz.

9. The method of claim 1, further comprising inserting the device into the instrument configured to determine whether the measured electrical property associated with the continuous polymer layer has exceeded the threshold level associated with the device usability.

10. The method of claim 1, where the device further comprises a sensor selected from the group consisting of a pH sensor, oxygen sensor, carbon dioxide sensor, hematocrit sensor, glucose sensor, lactate sensor, creatinine sensor, sodium sensor, potassium sensor, magnesium sensor, calcium sensor, chloride sensor, phosphate sensor, liver enzyme sensor, B-type Natriuretic Peptide (BNP) sensor, troponin sensor, blood urea nitrogen (BUN) sensor, creatine kinase myocardial b fraction (CKMB) sensor, neutrophil gelatinase associated lipocalin (NGAL) sensor, thyroid stimulating hormone (TSH) sensor, D-dimer sensor, prostate specific antigen (PSA) sensor, parathyroid hormone (PTH) sensor, cholesterol sensor, alanine transaminase (ALT) sensor, aspartate aminotransferase (AST) sensor, prothrombin sensor, activated partial thromboplastin time (APTT) sensor, activated clotting time (ACT) sensor, galectin sensor, and combinations thereof.

11. A method of determining device usability, comprising the steps of:
    providing a device comprising a first electrical pad; a second electrical pad; and a continuous polymer layer contacting at least a portion of the first and second electrical pads;
    applying, by an instrument, a potential across the first and second electrical pads;
    measuring, by the instrument, an electrical property associated with the continuous polymer layer;
    determining, by the instrument, whether the measured electrical property associated with the continuous polymer layer has exceeded a threshold level associated with the device usability; and
    determining, by the instrument, the device is valid for use when the measured electrical property associated with the continuous polymer layer does not exceed the threshold level,
    wherein the continuous polymer layer comprises a polymer matrix, a plasticizer and an organic salt, and
    wherein the continuous polymer layer comprises from 0.1 to 10 wt.% of the organic salt.

12. The method of claim 11, wherein the organic salt is selected from the group consisting of quaternary ammonium tetrakis phenylborate, dodecyl sulfosuccinate, lauryl sulfate, alkyl ether phosphates, benzylkonium, cetylpyrdinium dodecyl sulfosuccinate, lauryl sulfate, alkyl ether phosphates, tetramethylammonium, benzylkonium, cetylpyrdinium, an iodide, a bromide, a perchlorate, a zwitterionic compound, cocamidopropyl hydroxysultaine and quaternary ammonium borate.

13. A method of determining device usability, comprising the steps of:
providing a device comprising a first electrical pad; a second electrical pad; and a continuous polymer layer contacting at least a portion of the first and second electrical pads;
applying, by an instrument, a potential across the first and second electrical pads;
measuring, by the instrument, an electrical property associated with the continuous polymer layer;
determining, by the instrument, whether the measured electrical property associated with the continuous polymer layer has exceeded a threshold level associated with the device usability; and
determining, by the instrument, the device is valid for use when the measured electrical property associated with the continuous polymer layer does not exceed the threshold level,
wherein the continuous polymer layer comprises a polymer matrix, a plasticizer and an organic salt, and
wherein the continuous polymer layer is substantially circular and has a diameter of from about 20 μm to about 2 mm.

14. The method of claim 13, wherein the device further comprises a boundary structure for controlling the spreading of a dispensed polymer layer precursor to a predetermined region of the device.

15. The method of claim 13, wherein the device further comprises a boundary structure for controlling the spreading of a dispensed liquid to a predetermined region of the device, wherein the boundary structure comprises a ring intersecting said first and second contact pads.

16. The method of claim 13, wherein the first and second pads are separated by a distance of from about 10 μm to about 2 mm.

17. A method of determining device usability, comprising the steps of:
providing a device comprising a first electrical pad; a second electrical pad; and a continuous polymer layer contacting at least a portion of the first and second electrical pads;
applying, by an instrument, a potential across the first and second electrical pads;
measuring, by the instrument, an electrical property associated with the continuous polymer layer;
determining, by the instrument, whether the measured electrical property associated with the continuous polymer layer has exceeded a threshold level associated with the device usability; and
determining, by the instrument, the device is valid for use when the measured electrical property associated with the continuous polymer layer does not exceed the threshold level,
wherein the continuous polymer layer comprises a polymer matrix, a plasticizer and an organic salt,
wherein the first and second pads are separated by a distance of from about 10 μm to about 2 mm, and
wherein the continuous polymer layer is domed.

18. A method of determining device usability, comprising the steps of:
measuring an initial current value associated with a continuous polymer layer when a device is manufactured;
providing the device comprising a first electrical pad; a second electrical pad; and the continuous polymer layer contacting at least a portion of the first and second electrical pads;
applying, by an instrument, a potential across the first and second electrical pads;
measuring, by the instrument, an electrical property associated with the continuous polymer layer;
determining, by the instrument, whether the measured electrical property associated with the continuous polymer layer has exceeded a threshold level associated with the device usability; and
determining, by the instrument, the device is valid for use when the measured electrical property associated with the continuous polymer layer does not exceed the threshold level,
wherein the electrical property comprises current, and
wherein the threshold level is at least five times lower than initial current value.

19. A method of determining device usability, comprising the steps of:
measuring an initial impedance value associated with a continuous polymer layer when a device is manufactured;
providing the device comprising a first electrical pad; a second electrical pad; and the continuous polymer layer contacting at least a portion of the first and second electrical pads;
applying, by an instrument, a potential across the first and second electrical pads;
measuring, by the instrument, an electrical property associated with the continuous polymer layer;
determining, by the instrument, whether the measured electrical property associated with the continuous polymer layer has exceeded a threshold level associated with the device usability; and
determining, by the instrument, the device is valid for use when the measured electrical property associated with the continuous polymer layer does not exceed the threshold level,
wherein the electrical property comprises current, and
wherein the threshold level is at least five times greater than the initial impedance.

20. A device having a usability threshold, comprising a first electrical pad, a second electrical pad, and a continuous polymer layer contacting at least a portion of the first and second electrical pads,
wherein the continuous polymer layer has an electrical property associated with the device usability threshold,
wherein the continuous polymer layer comprises a polymer matrix, a plasticizer and an organic salt, and
wherein the continuous polymer layer comprises from 20 to 40 wt.% polymer matrix.

21. The device of claim 20, wherein the polymer matrix comprises a polymer selected from the group consisting of polyvinyl chloride (PVC), polyurethane, polyvinylacetate, carboxylated PVC, hydroxylated PVC and polydimethyl siloxane.

22. The device of claim 20, wherein the polymer layer comprises from 60 to 80% plasticizer.

23. The device of claim 20, wherein the plasticizer is selected from the group consisting of trioctyl phosphate (TOP), nitrophenyloctyl ether (NPOE), bisethylhexylsebacate (BEHS), trimethyl trimellitate (TMTT), dioctyl adipate (DOA) and diisobutyl phthalate (DIBP).

24. A device having a usability threshold, comprising
a first electrical pad, a second electrical pad, and a continuous polymer layer contacting at least a portion of the first and second electrical pads,
wherein the continuous polymer layer has an electrical property associated with the device usability threshold,
wherein the continuous polymer layer comprises a polymer matrix, a plasticizer and an organic salt, and
wherein the continuous polymer layer comprises from 0.1 to 10 wt.% of the organic salt.

25. The device of claim 24, wherein the organic salt is selected from the group consisting of quaternary ammonium tetrakis phenylborate, dodecyl sulfosuccinate, lauryl sulfate, alkyl ether phosphates, benzylkonium, cetylpyrdinium dodecyl sulfosuccinate, lauryl sulfate, alkyl ether phosphates, tetramethylammonium, benzylkonium, cetylpyrdinium, an iodide, a bromide, a perchlorate, a zwitterionic compound, cocamidopropyl hydroxysultaine and quaternary ammonium borate.

26. A device having a usability threshold, comprising
a first electrical pad, a second electrical pad, and a continuous polymer layer contacting at least a portion of the first and second electrical pads,
wherein the continuous polymer layer has an electrical property associated with the device usability threshold,
wherein the continuous polymer layer comprises a polymer matrix, a plasticizer and an organic salt, and
wherein the continuous polymer layer is substantially circular and has a diameter of from about 20 µm to about 2 mm.

27. The device of claim 26, further comprising a boundary structure for controlling the spreading of a dispensed polymer layer precursor to a predetermined region of the device.

28. The device of claim 26, further comprising a boundary structure for controlling the spreading of a dispensed liquid to a predetermined region of the device, wherein the boundary structure comprises a ring intersecting said first and second contact pads.

29. The device of claim 26, wherein the first and second pads are separated by a distance of from about 10 µm to about 2 mm.

30. A device having a usability threshold, comprising
a first electrical pad, a second electrical pad, and a continuous polymer layer contacting at least a portion of the first and second electrical pads,
wherein the continuous polymer layer has an electrical property associated with the device usability threshold,
wherein the continuous polymer layer comprises a polymer matrix, a plasticizer and an organic salt, and
wherein the continuous polymer layer is domed.

31. The device of claim 30, wherein the distance between the first and second electrical pads is from 10 µm to 2 mm.

32. The device of claim 30, further comprising a sensor selected from the group consisting of a pH sensor, oxygen sensor, carbon dioxide sensor, hematocrit sensor, glucose sensor, lactate sensor, creatinine sensor, sodium sensor, potassium sensor, magnesium sensor, calcium sensor, chloride sensor, phosphate sensor, liver enzyme sensor, B-type Natriuretic Peptide (BNP) sensor, troponin sensor, blood urea nitrogen (BUN) sensor, creatine kinase myocardial b fraction (CKMB) sensor, neutrophil gelatinase associated lipocalin (NGAL) sensor, thyroid stimulating hormone (TSH) sensor, D-dimer sensor, prostate specific antigen (PSA) sensor, parathyroid hormone (PTH) sensor, cholesterol sensor, alanine transaminase (ALT) sensor, aspartate aminotransferase (AST) sensor, prothrombin sensor, activated partial thromboplastin time (APTT) sensor, activated clotting time (ACT) sensor, galectin sensor, and combinations thereof.

33. A method of making a device having a usability threshold, comprising the steps of:
providing a substantially planar surface comprising a first electrical pad and a second electrical pad;
dispensing a polymer layer precursor onto the surface, and forming from the polymer layer precursor a continuous polymer layer contacting at least a portion of the first and second electrical pads,
wherein the continuous polymer layer has an electrical property associated with the device usability threshold,
wherein the continuous polymer layer comprises a polymer matrix, a plasticizer and an organic salt, and
wherein the continuous polymer layer comprises from 20 to 40 wt.% polymer matrix.

34. The method of claim 33, wherein the polymer layer precursor comprises an aqueous solution comprising polymer particles dispersed in water.

35. The method of claim 33, wherein the device further comprises a boundary structure that controls the region of the device where the liquid is dispensed.

36. The method of claim 35, wherein the boundary structure comprises a ring intersecting the first and second electrical pads.

37. A method of determining a threshold level associated with analytical device usability, comprising the steps of:
providing a plurality of devices, each of said devices comprising a sensor; a first electrical pad; a second electrical pad; and a continuous polymer layer contacting at least a portion of the first and second electrical pads, wherein said devices have been exposed to different environmental conditions;
measuring, by an instrument, an electrical property of the continuous polymer layer for each of the devices;
measuring, by the instrument, a sensor signal for a control fluid for each of the devices;
identifying, by the instrument, a subset of said plurality of devices that provide a signal having a predetermined acceptable precision level for said control fluid; and
determining, by the instrument, the threshold level based on an initial value of the electrical property of the continuous polymer layer of a subset of said plurality of devices,
wherein the continuous polymer layer comprises a polymer matrix, a plasticizer and an organic salt, and
wherein the continuous polymer layer comprises from 20 to 40 wt.% polymer matrix.

38. The method of claim 37, wherein the environmental conditions include variations in at least one of time, temperature, or humidity.

39. A device comprising a sensor and a continuous polymer layer formed on a substantially planar surface,
wherein the surface comprises two adjacent electrical contact pads and a space therebetween,
wherein said continuous polymer layer covers at least a portion of the two electrical contact pads and a portion of said space therebetween,
wherein a preselected potential or potential cycle is applied to the pads and the impedance or current associated with said continuous polymer layer is measured, said measured value is converted to a value indicative of the average shelf life time remaining for other devices from the same manufacturing lot, wherein the continuous polymer layer comprises a polymer matrix, a plasticizer and an organic salt, and
wherein the continuous polymer layer comprises from 20 to 40 wt.% polymer matrix.

* * * * *